Figure 1A:
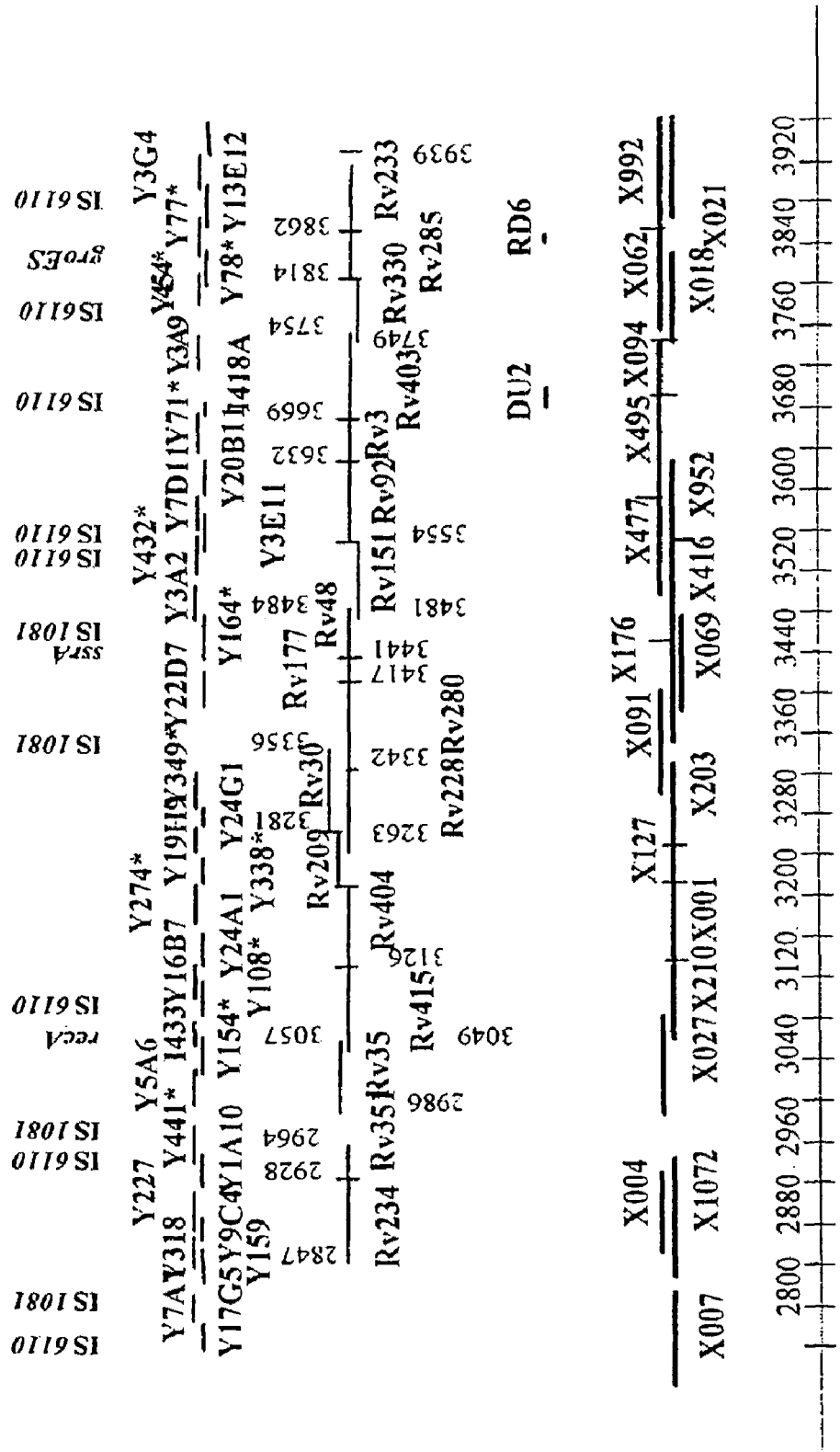
Figure 1B:
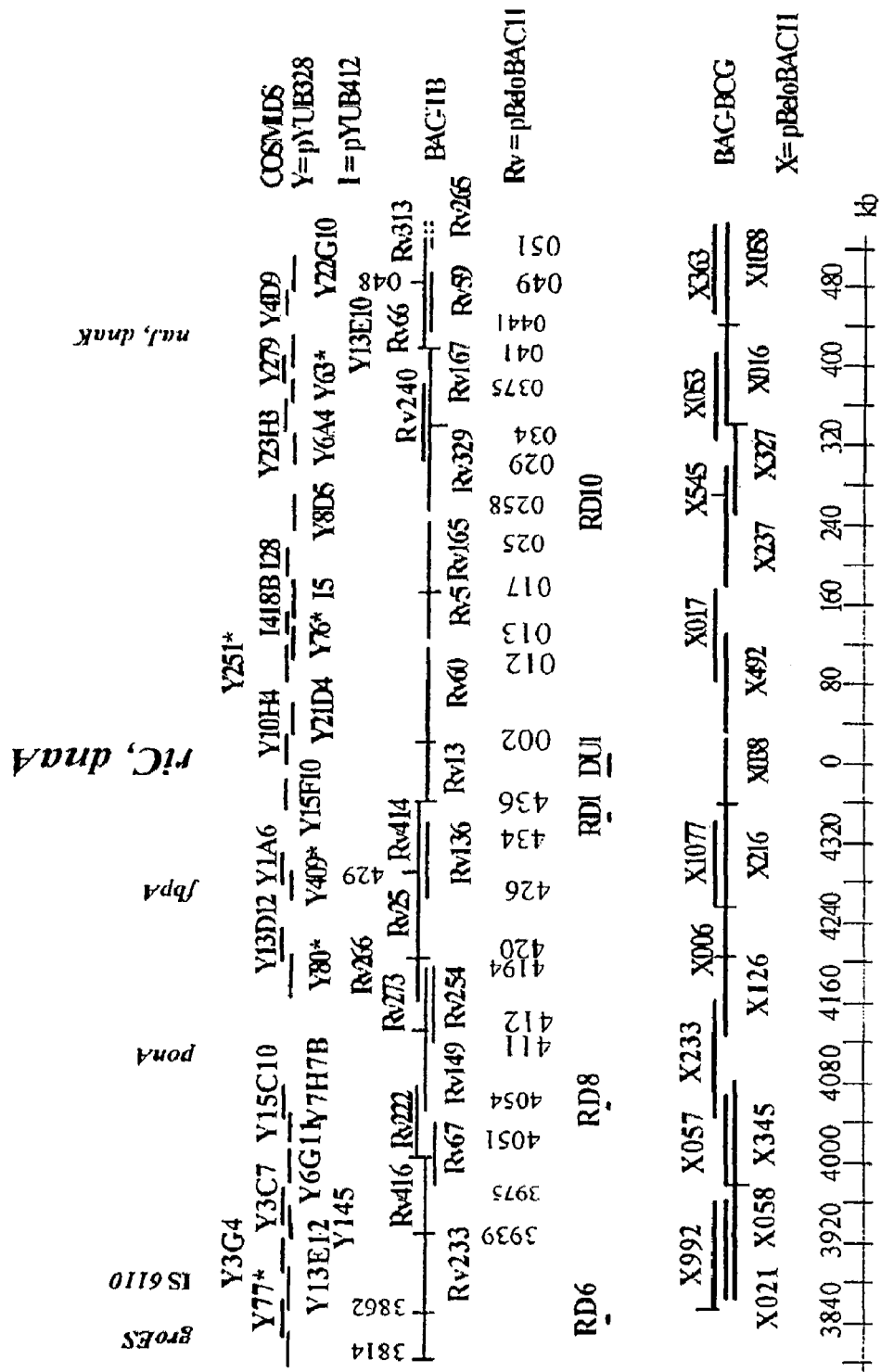
Figure 1C:
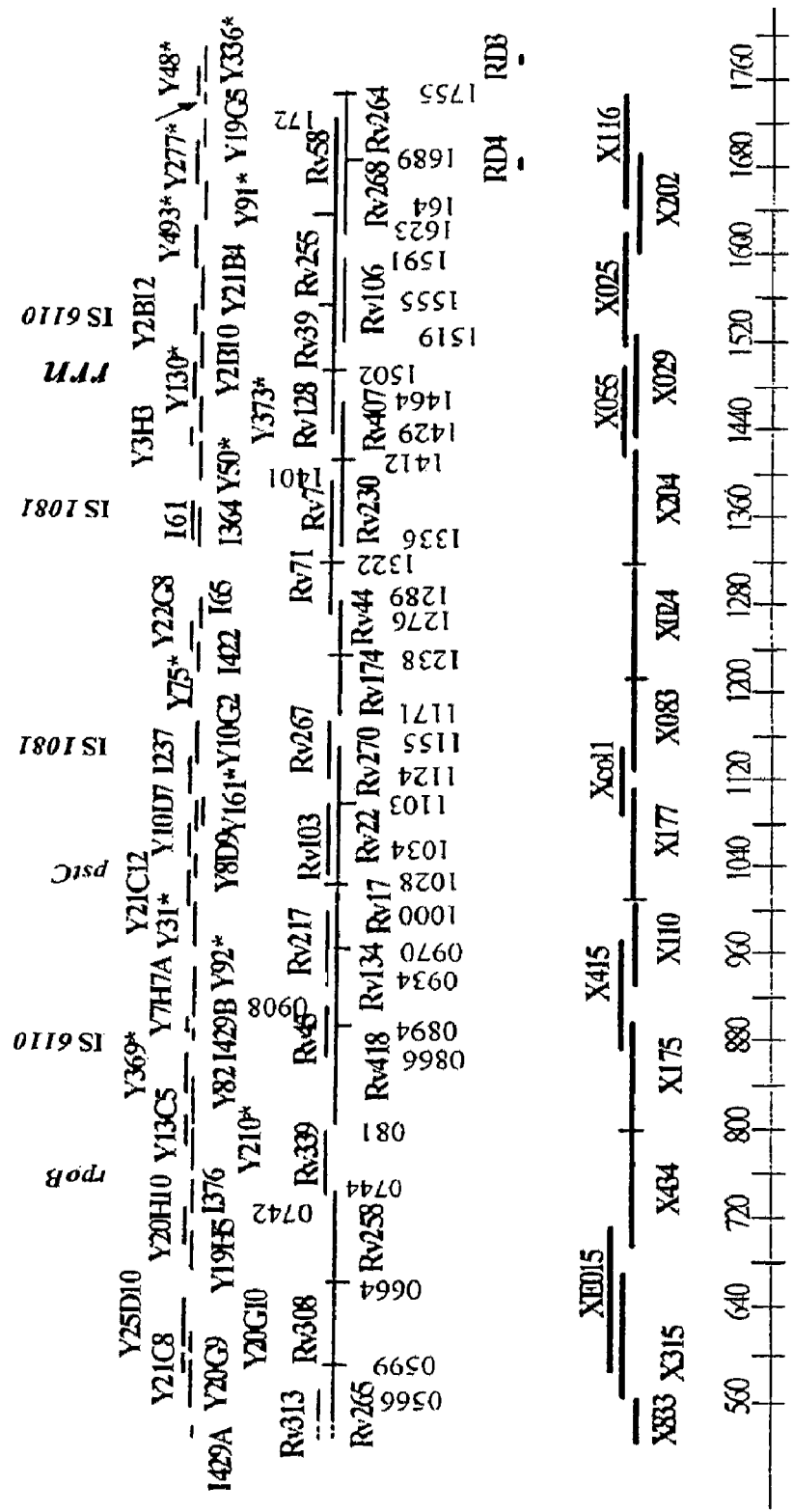
Figure 1D:
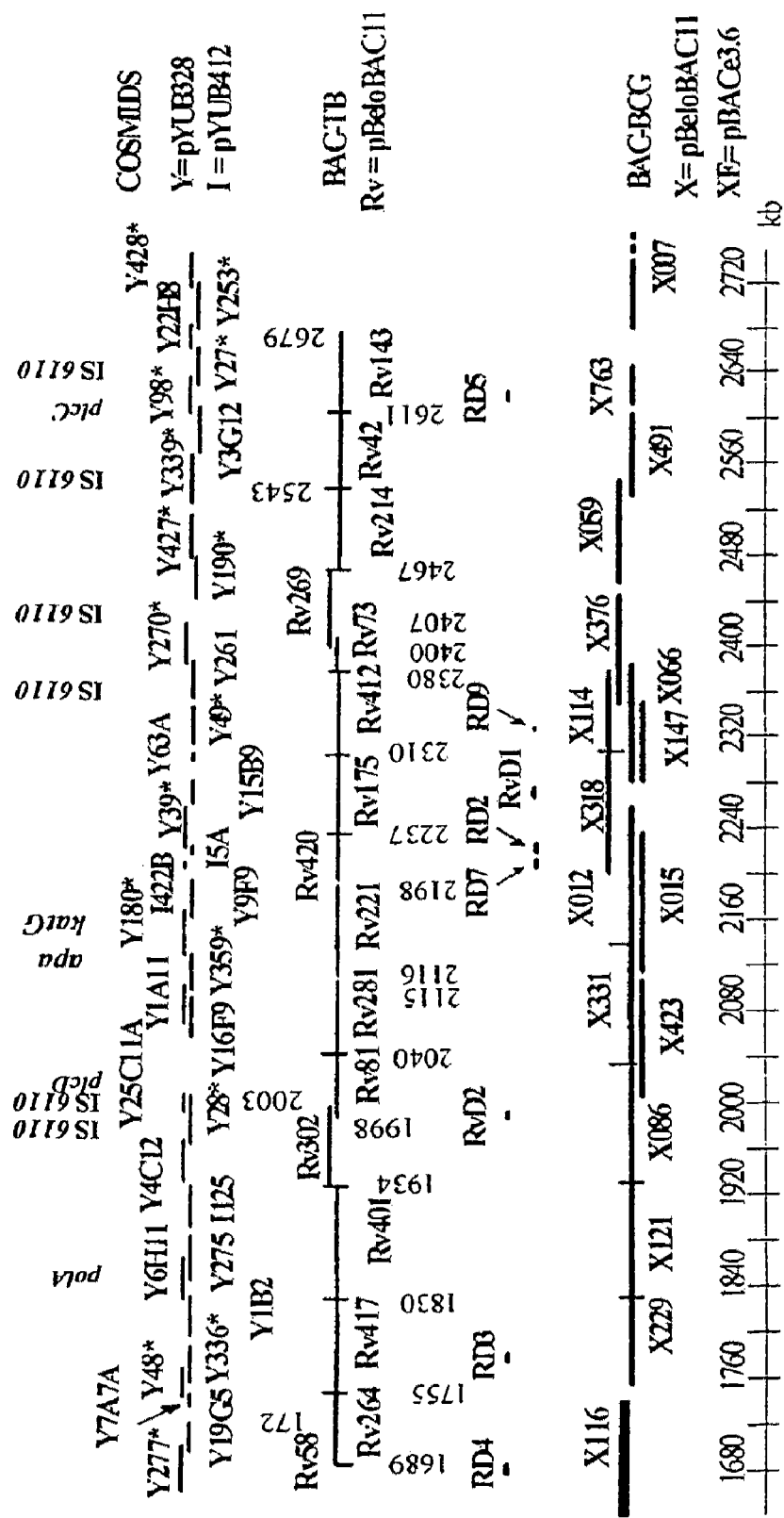
Figure 2A:
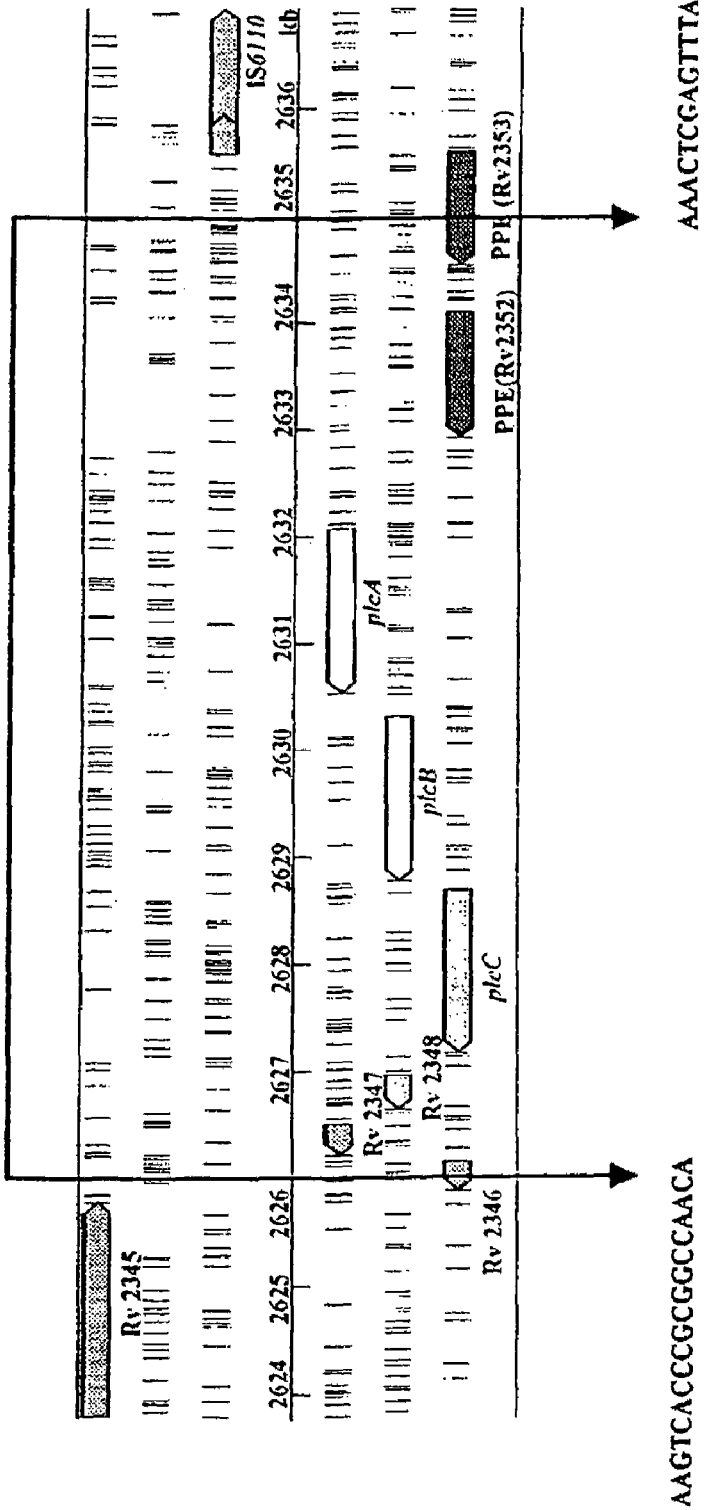
Figure 2B:
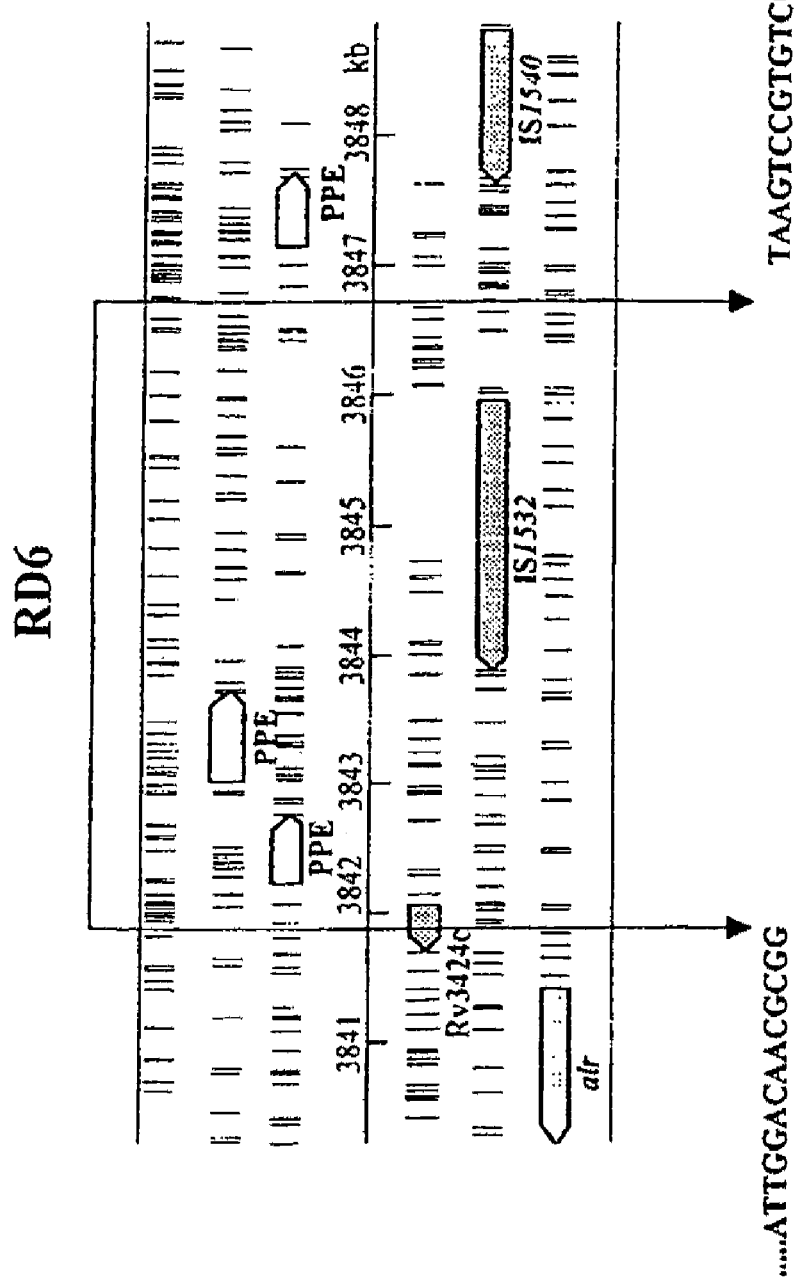
Figure 2C:
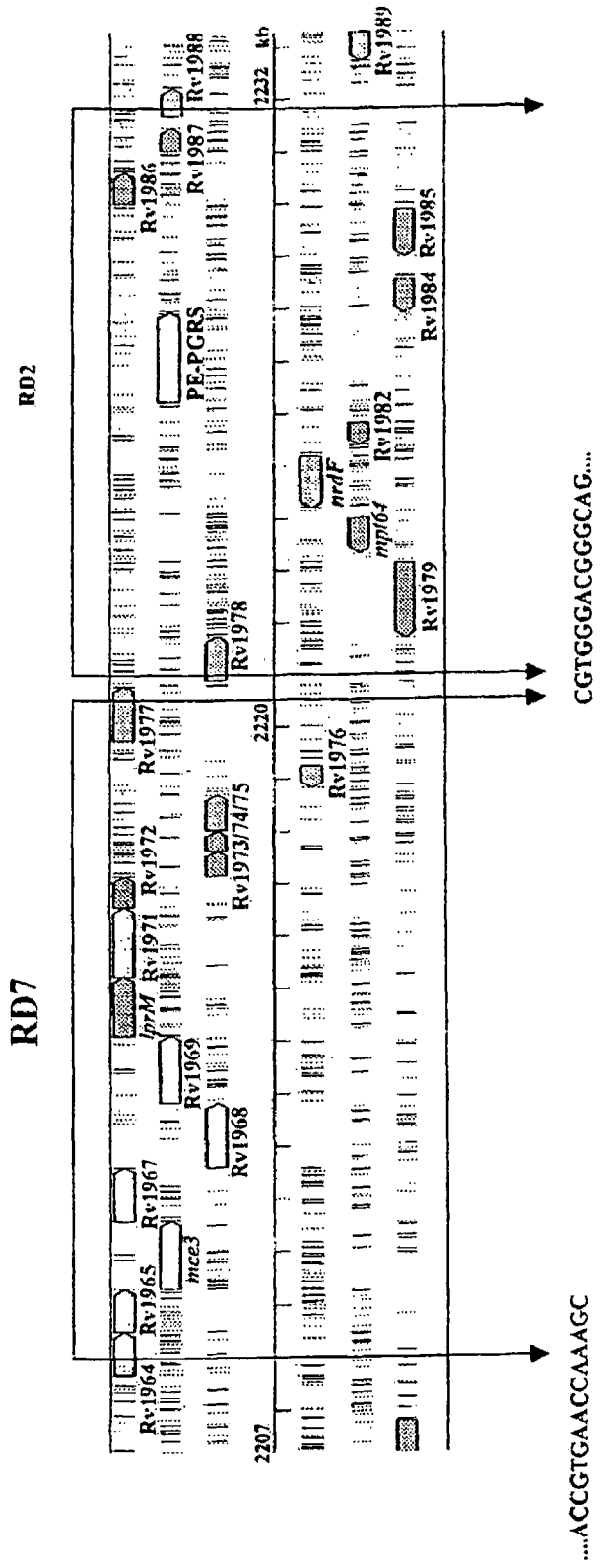
Figure 2D:
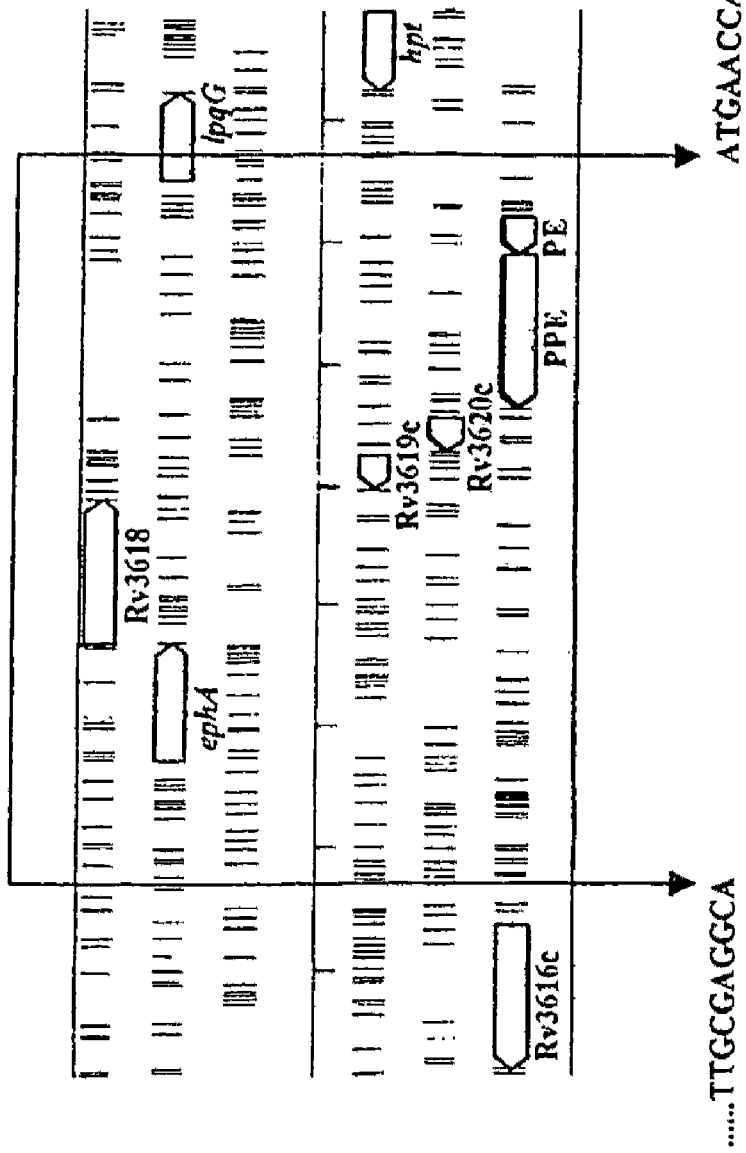
Figure 2E:
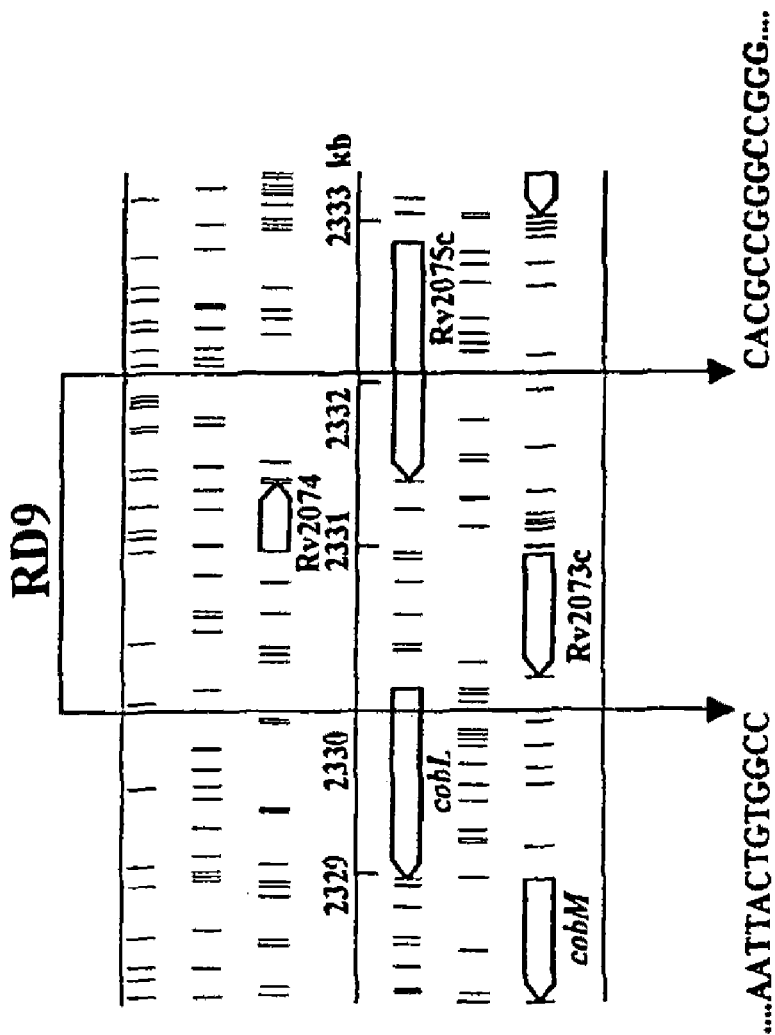
Figure 2F:
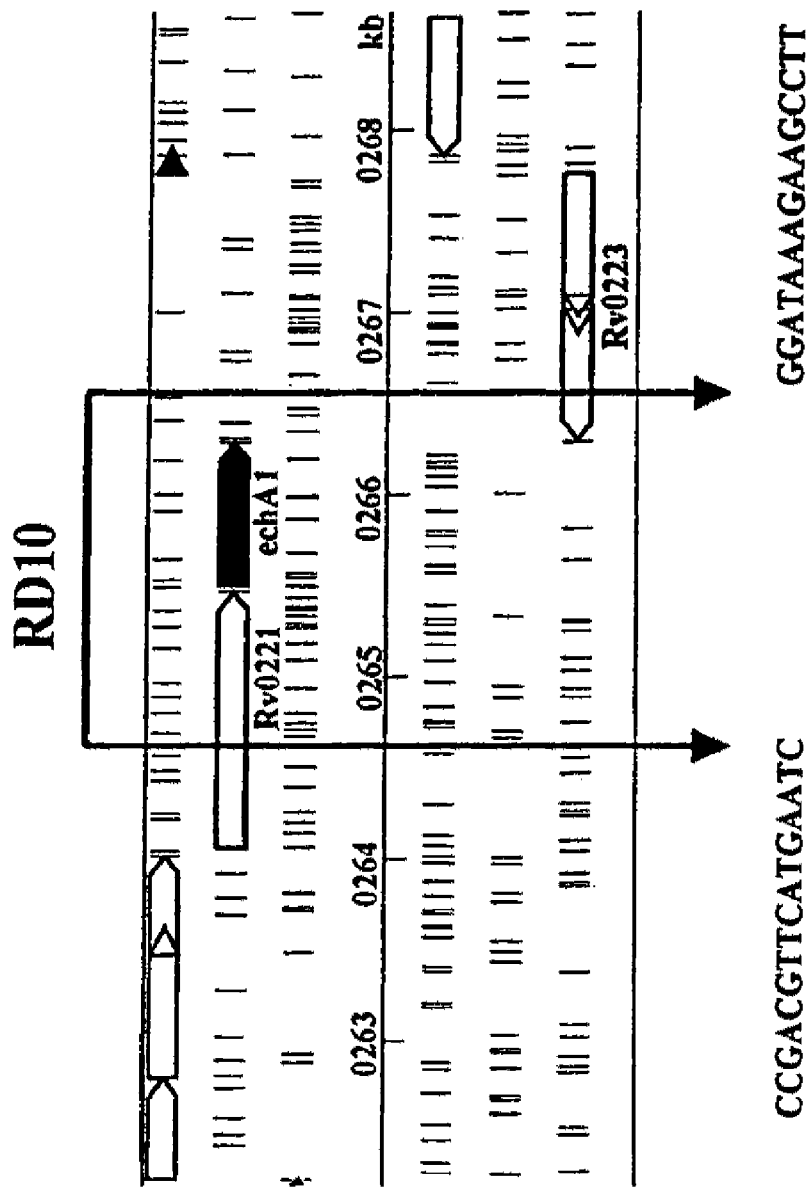
Figure 3:
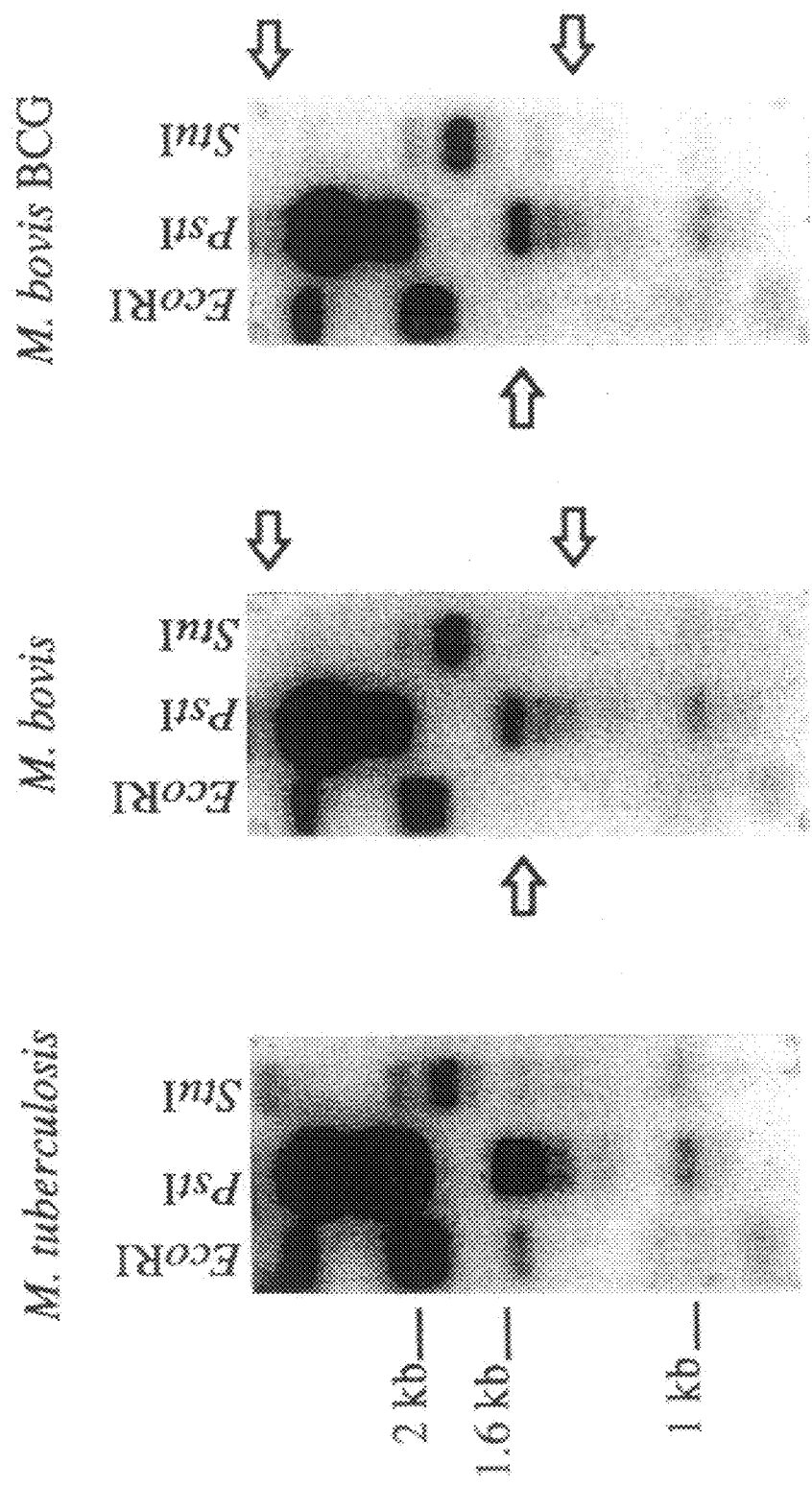

US008357493B2

(12) United States Patent
Cole et al.

(10) Patent No.: US 8,357,493 B2
(45) Date of Patent: Jan. 22, 2013

(54) **METHOD FOR DETECTING MYCOBACTERIA USING DELETED SEQUENCES IN *M. BOVIS* BCG/*M. BOVIS* OR TUBERCULOSIS**

(75) Inventors: Stewart Cole, Clamart (FR); Stéphen Gordon, Guildford (GB); Roland Buchrieser-Brosch, Paris (FR); Alain Billault, Roissy-en-Brie (FR); Thierry Garnier, Ermont (FR)

(73) Assignee: Institut Pasteur, Paris (FR)

( * ) Notice: Subject to any disclaimer, the term of this patent is extended or adjusted under 35 U.S.C. 154(b) by 1066 days.

(21) Appl. No.: 10/980,194

(22) Filed: Nov. 4, 2004

(65) Prior Publication Data

US 2005/0250120 A1 Nov. 10, 2005

Related U.S. Application Data

(63) Continuation of application No. 09/936,523, filed as application No. PCT/FR00/00637 on Mar. 16, 2000, now abandoned.

(30) Foreign Application Priority Data

Mar. 16, 1999 (FR) ..................................... 99 03250

(51) Int. Cl.
*C12Q 1/68* (2006.01)
*C07H 21/04* (2006.01)

(52) U.S. Cl. ................... 435/6.15; 435/6.12; 536/24.32; 536/24.33

(58) Field of Classification Search ........................ None
See application file for complete search history.

(56) References Cited

U.S. PATENT DOCUMENTS

| | | | | |
|---|---|---|---|---|
| 5,656,493 | A * | 8/1997 | Mullis et al. ............... | 435/286.1 |
| 6,291,190 | B1 * | 9/2001 | Behr et al. ...................... | 435/7.1 |
| 6,294,328 | B1 * | 9/2001 | Fleischmann et al. ............ | 435/6 |

FOREIGN PATENT DOCUMENTS

| | | | |
|---|---|---|---|
| EP | 0 461 045 A1 | 12/1991 |
| WO | WO 99/54487 | 10/1999 |

OTHER PUBLICATIONS

Ruano, G. et al. Nucleic Acids Research 19(24):6877-6882 (1999).*
Brosch, R. et al., "Use of a *Mycobacterium tuberculosis* H37Rv Bacterial Artificial Chromosome Library for Genome Mapping, Sequencing, and Comparative Genomics," *Infection and Immunity*, vol. 66, No. 5, pp. 2221-2229 (1998).
Cole et al., "Deciphering the Biology of *Mycobaterium tuberculosis* from the Complete Genome Sequence," *Nature*, vol. 393, pp. 537-544 (1998).

(Continued)

*Primary Examiner* — Diana Johannsen
(74) *Attorney, Agent, or Firm* — Finnegan, Henderson, Farabow, Garrett & Dunner, LLP

(57) ABSTRACT

The invention concerns the isolation of nucleotide and peptide sequences in particular for differentiating, in diagnostic terms, an immunization resulting from BCG vaccination of an infection by *M. tuberculosis*. Said sequences are either *M. bovis* BCG/*M. bovis* specific or *M. tuberculosis* specific. The invention also concerns a method for detecting said sequences, a method for detecting antibodies generated by the products expressing said sequences as well as kits for implementing said methods. Finally, the invention concerns novel vaccines.

9 Claims, 15 Drawing Sheets

OTHER PUBLICATIONS

Gordon, S.V. et al., "Identification of Variable Regions in the Genomes of Tubercle Bacilli Using Bacterial Artificial Chromosome Arrays," *Molecular Microbiology*, vol. 32, No. 2, pp. 643-655 (1999).

Harboe, et al., "Homology Between the MPB70 and MPB83 Proteins of *Mycobacterium bovis* BCG, Scand.," *J. Immuno.* vol. 42, pp. 46-51 (1995).

Harboe, et al., "Evidence for Occurrence of the ESAT-6 Protein in *Mycobacterium tuberculosis* and Virulent *Mycobacterium bovis* and for Its Absence in *Mycobacterium bovis* BCG," *Infection and Immunity*, vol. 64, pp. 16-22 (1996).

Harboe, et al., "B-Cell Epitopes and Quantification of the ESAT-6 Protein of *Mycobacterium tuberculosis*," *Infection and Immunity*, vol. 66, pp. 717-723 (1998).

Horwitz, et al., "Protective Immunity Against Tuberculosis Induced by Vaccination with Major Extracellular Proteins of *Mycobacterium tuberculosis*," *Proc. Nat'l. Acad. Sci.*, vol. 92, pp. 1530-1534 (1995).

Lagranderi, et al., "Comparison of Immune Responses of Mice Immunized with Five Different *Mycobacterium bovis* BCG Vaccine Strains," Infection and Immunity, vol. 64, pp. 1-9 (1996).

Mahairas et al., "Molecular Analysis of Genetic Differences Between *Mycobacterium bovis* BCG and Virulent *M. bovis*," *J. Bacteriol.*, vol. 178, pp. 1274-1282 (1996).

Philipp, et al., Physical Mapping of *Mycobacterium bovis* BCG Pasteur Reveals Differences from the Genome Map of *Mycobacterium tuberculosis* H37Rv and from *M. bovis, Microbiology*, vol. 142, pp. 3135-3145 (1996).

International Search Report for PCT/FR00/00637, dated Jul. 27, 2000.

* cited by examiner

METHOD FOR DETECTING MYCOBACTERIA USING DELETED SEQUENCES IN *M. BOVIS* BCG/*M. BOVIS* OR TUBERCULOSIS

This is a continuation of application Ser. No. 09/936,523, filed Sep. 14, 2001, now abandoned which is a 371 of Application No. PCT/FR00/00637, filed Mar. 16, 2000, and claims the priority of FR 99003250, filed Mar. 16, 1999, all of which are incorporated herein by reference.

The subject of the present invention is the identification of nucleotide sequences which make it possible in particular to distinguish, in diagnostic terms, an immunization resulting from a BCG vaccination from an *M. tuberculosis* infection. The sequences in question are specific either to *M. bovis* BCG/*M. bovis*, or to *M. tuberculosis*. The subject of the present invention is also a method for detecting the sequences in question, a method for detecting antibodies generated by the products of expression of these sequences and the kits for carrying out these methods. Finally, the subject of the present invention is novel vaccines.

The high rate of mortality and morbidity caused by *Mycobacterium tuberculosis*, the etiological agent for tuberculosis, brings about the need to develop novel vaccines and ever shorter chemotherapeutic treatments. Indeed, the appearance of *M. tuberculosis* strains resistant to antituberculars and the increased risk in immunosuppressed patients, for example in AIDS patients, of developing tuberculosis, necessitates the development of rapid, specific and reliable methods for the diagnosis of tuberculosis and the development of novel vaccines. The conventional BCG vaccine is derived from a *Mycobacterium bovis* strain which was attenuated by repeated serial passages on bile potato-glycerinox agar (Calmette, 1927; Bloom and Fine, 1994). However, in spite of almost 50 years of worldwide use, the reason for the attenuation of *M. bovis* BCG is still unknown. Questions remain as regards the protection conferred by the vaccine against pulmonary tuberculosis, with an efficacy of between 0 and 80% (Fine, 1994). Furthermore, many BCG substrains exist and offer various levels of protection against tuberculosis in a mouse model (Lagranderie et al., 1996). The attenuation of the original *M. bovis* strain may have been caused by mutations in the genome of the *bacillus* which were selected during serial passages of the strain, which mutations remained stable in the genome. However, as the original *M. bovis* strain has been lost, direct comparison between it and *M. bovis* BCG is impossible. In spite of that, the identification of genetic differences between *M. bovis*, *M. bovis* BCG and *M. tuberculosis* is likely to reveal locations whose alteration may have led to the attenuation of *M. bovis* BCG.

The *M. tuberculosis* DNA has more than 99.9% homology with the DNA of the other members of the tuberculous complex (*M. bovis, M. microtis, M. africanum*). Although closely related, these strains may be differentiated on the basis of their host range, their virulence for humans and their physiological characteristics (Heifets and Good, 1994). As in the case of the attenuation of BCG, the genetic base for the phenotypic differences between the tubercle bacilli is mainly unknown. However, the wealth of information contained in the genomic sequence of *M. tuberculosis* H37Rv led to the thought that the genetic variations between the strains was going to be revealed (Cole et al., 1998). Genomic comparison presents a powerful tool for such research studies since the whole genomes may be studied in preference to the study of genes in their individual forms. A previous comparative study of *M. bovis* and *M. bovis* BCG by substractive genomic hybridization has shown that three regions, designated RD1, RD2 and RD3, were deleted in *M. bovis* BCG compared to *M. bovis* (Mahairas et al., 1996). However, the role, where appropriate, of these regions in the attenuation of *M. bovis* BCG has not been clearly established. Similarly, other studies of genomic differences between *M. bovis*, *M. bovis* BCG and *M. tuberculosis* have shown that many polymorphic locations existed between these strains (Philipp et al., 1996). Although the exact nature of these polymorphisms has not been elucidated, additional analyses have revealed that a polymorphism was due to the deletion of 12.7 kb in *M. bovis* and BCG compared to *M. tuberculosis* (Brosch et al., 1998). From that, it appears that there are two classes of deletion: those which are absent from BCG but present in *M. bovis* and *M. tuberculosis* and those which are absent from *M. bovis* and BCG but present in *M. tuberculosis*.

The bacterial artificial chromosome (BAC) library for *M. tuberculosis* H37Rv deposited at the CNCM under No. 1-1945 on Nov. 19, 1997 and described in application WO9954487 demonstrates complete knowledge of the genomic sequence of *M. tuberculosis* and presents a potential as a tool for postgenomic applications such as genomic comparisons (Brosch et al., 1998). To push the investigations into the genomic differences between *M. tuberculosis* and *M. bovis* BCG even further, the inventors prepared a BAC library from *M. bovis* BCG deposited on Jun. 30, 1998 at the CNCM under No. 1-2049 and described in application WO9954487. This type of library indeed has certain advantages. Firstly, the BAC system can maintain large inserts of mycobacterial DNA, up to 120 kb. The 4.36 Mb of *M. bovis* BCG genome could therefore be represented in 50 to 60 clones, simplifying the storage and handling of the library. Secondly, the BAC system can allow, in complete confidence, replication of the inserts without genericing rearrangement or deletion in the clones. From that, alterations of the insert cannot be at the origin of an error for the duration in the genome. Thirdly, the positioning of the BAC clones on the *M. bovis* BCG chromosome is likely to generate a map of clones which overlap, which ought to allow direct comparison of the local segments on the *M. tuberculosis* and *M. bovis* BCG genome, while being a resource of interest for the sequencing of the *M. bovis* BCG genome.

The construction of a BAC library for *M. bovis* BCG-Pasteur (1-2049) is described below as well as its use, in conjunction with the BAC library for *M. tuberculosis* H37Rv (1-1945), as a tool for genomic comparison. With this approach, the inventors have been able to identify novel deletions and insertions between the tubercle bacilli, which makes it possible to have a picture in two genomes of the dynamics and differentiation in the *M. tuberculosis* complex.

The main route for extracting biological information from the genome is the comparison between the genomes. The technology of biochips or "DNA chips" (Chee et al., 1996; DeRisi et al., 1997) described, for example, in patents No. WO97/02357 and No. WO97/29212 makes it possible to make alignments and to select the sequences of interest. However, the availability of a minimum set of BAC clones for the genomes of *M. bovis* BCG and *M. tuberculosis* H37Rv has offered the inventors ready-to-use tools for the abovementioned comparative studies. The BAC library for *M. bovis* BCG contains more than 1500 clones with an average size of inserts of about 75 kb. 57 clones cover the BCG genome including a HindIII fragment of 120 kb which was absent from the *M. tuberculosis* BAC library. The construction of BAC chips from the *M. bovis* BCG library should allow the inventors to extend their comparative studies relating to the tubercle *bacillus*. These fragments can be hybridized with the genomic DNA from clinical isolates from *M. tuberculosis* or epidemic strains in order to identify other deletions or rearrangements, and from that, allow a novel picture relating to the plasticity of the genome as well as the identification of the genes and the gene products which may be involved in the virulence.

At the end of the experiments reported here, the inventors identified 10 locations or loci which are absent from *M. bovis* BCG compared to *M. tuberculosis*. Hybridizations with the genomic DNA of *M. bovis* revealed that 7 of these loci were also deleted in *M. bovis* compared to *M. tuberculosis*. Thus, in the text below, every time reference is made to the characteristics common to the genome of *M. bovis* BCG and to that of *M. bovis* it will be indicated that this means the "genome of *M. bovis* BCG/*M. bovis*".

It was then found that 3 of the specific deletions which appeared in *M. bovis* BCG were identical to the RD1, RD2 and RD3 regions defined by the Stover team (Mahairas et al., 1996). Thus, by retaining the preceding nomenclature the inventors called the other 7 deletions of the *M. bovis* BCG/*M. bovis* genome, RD4, RD5, RD6, RD7, RD8, RD9 and RD10.

Other deletions have been found to be specific to the *M. tuberculosis* genome, it being understood that the "corresponding" sequences were present in *M. bovis* BCG/*M. bovis*; they were called RvD1 and RvD2 (tables 1 and 2).

The RD5-RD10, RvD1 and RvD2 deletions allowed the inventors to identify thoroughly the dynamics of the genome in the tubercle *bacillus* and gave information relating to the genetic bases of the phenotypic differentiation of the complex. The identification of RvD1 and RvD2 as deletions of the *M. tuberculosis* H37Rv genome shows that the deletion process does not function in a single direction, and the loss of information can therefore occur both in bovine strains and in human strains. It is observed that 8 of the deletions detected are located in a region of the chromosome where termination of replication probably occurs.

The inventors then, within each deleted region, identified several ORFs (or open reading frames) or genes and they tried to determine the putative function of each of them (table 1).

The subject of the present invention is therefore nucleotide sequences deleted from the genome of *M. bovis* BCG/*M. bovis* and present in the genome of *M. tuberculosis* or conversely chosen from the following ORFs and genes: Rv2346c, Rv2347c, Rv2348c, plcC, plcB, plcA, Rv2352c, Rv2353c, Rv3425, Rv3426, Rv3427c, Rv3428c, Rv1964, Rv1965, mce3, Rv1967, Rv1968, Rv1969, lprM, Rv1971, Rv1972, Rv1973, Rv1974, Rv1975, Rv1976c, Rv1977, ephA, Rv3618, Rv3619c, Rv3620c, Rv3621c, Rv3622c, lpgG, cobL, Rv2073c, Rv2074, Rv2075, echA1, Rv0223c, RvD1-ORF1, RvD1-ORF2, Rv2024c, plcD, RvD2-ORF1, RvD2-ORF2, RvD2-ORF3, Rv1758.

The expression "nucleotide sequence" according to the present invention is understood to mean a double-stranded DNA, a single-stranded DNA and products of transcription of said DNAs.

More particularly, the nucleotide sequences listed above are grouped into nucleotide regions according to the following distribution:

RD5: Rv2346c, Rv2347c, Rv2348c, plcC, plcB, picA, Rv2352c, Rv2353c,
RD6: Rv3425, Rv3426, Rv3427c, Rv3428c,
RD7: Rv1964, Rv1965, mce3, Rv1967, Rv1968, Rv1969, lprM, Rv1971, Rv1972, Rv1973, Rv1974, Rv1975, Rv1976c, Rv1977,
RD8: ephA, Rv3618, Rv3619c, Rv3620c, Rv3621c, Rv3622c, lpgG,
RD9: cobL, Rv2073c, Rv2074, Rv2075,
RD10: echA1, Rv0223c,
RvD1: RvD1-ORF1, RvD1-ORF2, Rv2024c
RvD2: plcD, RvD2-ORF1, RvD2-ORF2, RvD2-ORF3, Rv1758.

Advantageously, 3 of the deletions (RD5, RD6 and RD8) contain 6 genes encoding PE and PPE proteins. As it has been suggested that these proteins have a possible role in antigenic variation (Cole et al., 1998), it can be deduced therefrom that these loci may represent sites of hypervariability between the tubercle strains.

At least 9 proteins capable of being exported or exposed at the surface are encoded by RD4 to RD10, which indicates that these polypeptides perhaps have a major role in the immune recognition of the *bacillus*. It has indeed been shown that secreted polypeptides can have a potential stimulatory role in the immune system and they are capable of playing a role of antigens known to become involved during the early stage of infection (Elhay et al., 1998; Horwitz et al., 1995; Rosenkrands et al., 1998).

The fact that RD5 and RD6 contain genes encoding proteins belonging to the ESAT-6 family, 14 of which are organized into 11 distinct loci, is particularly significant (F. Tekaia, S. Gordon, T. Garnier, R. Brosch, B. G. Barrell and S. T. Cole, submitted). ESAT-6 is a major T cell antigen which appears to be secreted by the virulent tubercle *bacillus* independently of the signal peptide (Harboe et al., 1996). It accumulates in the extracellular medium during the early phases of growth and its gene is located in RD1, a region which is deleted from the genome of *M. bovis* BCG (Mahairas et al., 1996; Philipp et al., 1996). 3 of the 10 RD regions thus contain genes of the ESAT-6 family, which indicates that other sites of ESAT-6 genes can also give rise to deletions or rearrangements.

The genomic sequence of *M. tuberculosis* H37Rv has moreover revealed the presence of 4 highly related genes encoding phospholipase C enzymes called plcA, plcB, plcC and plcD (Cole et al., 1998). Phospholipase C has been recognized as a major virulence factor in a number of bacteria including *Clostridum perfringens, Listeria monocytogenes* and *Pseudomonas aeruginosa* where it plays an intracellular role in the dissemination of bacterial cells, in intracellular survival and in cytolysis (Titball, 1993). The RD5 deletion includes 3 genes (plcA, plcB and plcC), this region being absent from *M. bovis, M. bovis* BCG and *M. microti*. The detection of the phospholipase activity in *M. tuberculosis, M. microti* and *M. bovis* but not in *M. bovis* BCG has been previously described in (Johansen et al., 1996; Wheeler and Ratledge, 1992) as well as the role of the enzymes encoded by plcA and plcB (also known under the name mpcA and mpcB) in the hydrolysis both of phosphatidylcholine and sphingomyelin. The levels of phospholipase C activity which are detected in *M. bovis* are considerably less than those observed in *M. tuberculosis* which are in agreement with the loss of plcABC, the sphingomyelinase activity still being detectable. The sequence data presented here show that full-length phospholipase is encoded by the plcD gene in *M. bovis* BCG-Pasteur and that its considerable sequence similarity with the products of plcA and plcB indicates that it is probably endowed both with phospholipase activity and with a sphingomyelinase activity. It is therefore probable that plcD may be responsible for the residual phospholipase C activity in strains exhibiting the RD5 deletion, such as *M. bovis*, although it is difficult to link this interpretation to the observed absence of phospholipase C in spite of the presence of sphingomyelinase in the *M. bovis* BCG strain used in other studies (Johansen et al., 1996; Wheeler and Raledge, 1992). Studies of expression with the cloned plcD gene ought to clarify this point.

The mce gene has been described by the Riley team as encoding a putative protein of *M. tuberculosis* of the invasin type, whose expression in *E. coli* allows the invasion of HeLa cells (Arruda et al., 1993). Three other Mce proteins have been identified as part of the genome sequencing project with their gene occupying the same position in the four large highly conserved operons comprising at least eight genes (Cole et al., 1998; Harboe et al., 1996). It is difficult to deduce the effects of the loss of mce3 (RD7) on *M. bovis, M. microti* and *M. bovis* BCG because of the fact that the remaining three copies of mce could complement any loss of activity, unless the operons are differently expressed. However, it is of interest to note that RD7 is absent from certain members of the *M. tuberculosis* complex which are not virulent for humans, suggesting that RD7 can play a specific role in human disease.

The genome of *M. tuberculosis* H37Rv also encodes six proteins (Eph-A-F) which show similarity with epoxide hydrolases whereas at least 21 enoyl-CoA hydratases (EchAl-21) and multiple aldehyde dehydrogenases are present (Cole et al., 1998). The loss of ephA (RD8), echA1 and the aldehyde dehydrogenase encoded by Rv0223c (RD10) in *M. bovis* BCG/*M. bovis* can therefore be compensated by other enzymes although the substrate specificity of the *M. tuberculosis* enzymes is unknown. The epoxide hydrolases are generally considered as detoxifying enzymes; a recent report has again showed that they play a role in the activation of leukotoxins (Moghaddam et al., 1997), a toxic fatty acid produced by the leukocytes which are involved in respiratory distress syndrome in adults. However, the question of knowing if the *M. tuberculosis* epoxide hydrolases can chemically modify host chemokines is without response. Alternatively, they can play a role in lipid detoxification of the products of peroxidation which are generated by oxygen radicals from activated macrophages.

RD9 is a region deleted from the genomes of *M. africanum, M. bovis, M. bovis* BCG and *M. microti* compared to *M. tuberculosis*. Consequently, in contrast to the other RD regions, the location of *M. africanum* is close to *M. bovis*, which indicates the presence of this strain between *M. tuberculosis* and *M. bovis* (Heifets and Good, 1994). Similarly, the RD4 region can differentiate *M. microti* from the bovine strains (table 2).

The proteins encoded by RD4 to RD10 can therefore have antigens of interest, allowing discrimination between individuals vaccinated with BCG and patients infected with *M. tuberculosis*.

Thus, the subject of the present invention is also a method for the discriminatory detection and identification of *M. bovis* BCG/*M. bovis* or *M. tuberculosis* in a biological sample, comprising the following steps:
   a) isolation of the DNA from the biological sample to be analyzed or production of a cDNA from the RNA of the biological sample,
   b) detection of the DNA sequences of the mycobacterium present in said biological sample,
   c) analysis of said sequences.

Preferably, in the context of the present invention, the biological sample consists of a fluid, for example human or animal serum, blood, a biopsy, bronchoalveolar fluid or pleural fluid.

Analysis of the desired sequences may, for example, be carried out by agarose gel electrophoresis. If the presence of a DNA fragment migrating to the expected site is observed, it can be concluded that the analyzed sample contained microbacterial DNA. This analysis can also be carried out by the molecular hybridization technique using a nucleic probe. This probe will be advantageously labeled with a nonradioactive (cold probe) or radioactive element.

Advantageously, the detection of the mycobacterial DNA sequences will be carried out using nucleotide sequences complementary to said DNA sequences. By way of example, they may include labeled or nonlabeled nucleotide probes; they may also include primers for amplification.

The amplification technique used may be PCR but also other alternative techniques such as the SDA (Strand Displacement Amplification) technique, the TAS technique (Transcription-based Amplification System), the NASBA (Nucleic Acid Sequence Based Amplification) technique or the TMA (Transcription Mediated Amplification) technique.

The primers in accordance with the invention have a nucleotide sequence chosen from the group comprising SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, and SEQ ID No. 18 with:
   the pair SEQ ID No. 1/SEQ ID No. 2 specific for RD4,
   the pair SEQ ID No. 3/SEQ ID No. 4 specific for RD5,
   the pair SEQ ID No. 5/SEQ ID No. 6 specific for RD6,
   the pair SEQ ID No. 7/SEQ ID No. 8 specific for RD7,
   the pair SEQ ID No. 9/SEQ ID No. 10 specific for RD8,
   the pair SEQ ID No. 11/SEQ ID No. 12 specific for RD9,
   the pair SEQ ID No. 13/SEQ ID No. 14 specific for RD10,
   the pair SEQ ID No. 15/SEQ ID No. 16 specific for RvD1, and
   the pair SEQ ID No. 17/SEQ ID No. 18 specific for RvD2, In a variant, the subject of the invention is also a method for the discriminatory detection and identification of *M. bovis* BCG/*M. bovis* or *M. tuberculosis* in the biological sample comprising the following steps:
   a) bringing the biological sample to be analyzed into contact with at least one pair of primers as defined above, the DNA contained in the sample having been, where appropriate, made accessible to the hybridization beforehand,
   b) amplification of the DNA of the mycobacterium,
   c) visualization of the amplification of the DNA fragments.

The amplified fragments may be identified by agarose or polyacrylamide gel electrophoresis by capillary electrophoresis or by a chromatographic technique (gel filtration, hydrophobic chromatography or ion-exchange chromatography). The specification of the amplification may be controlled by molecular hybridization using probes, plasmids containing these sequences or their product of amplification.

The amplified nucleotide fragments may be used as reagent in hybridization reactions in order to detect the presence, in a biological sample, of a target nucleic acid having sequences complementary to those of said amplified nucleotide fragments.

These probes and amplicons may be labeled or otherwise with radioactive elements or with nonradioactive molecules such as enzymes or fluorescent elements.

The subject of the present invention is also a kit for the discriminatory detection and identification of *M. bovis* BCG/*M. bovis* or *M. tuberculosis* in a biological sample comprising the following components:
   a) at least one pair of primers as defined above,
   b) the reagents necessary to carry out a DNA amplification reaction,
   c) optionally, the necessary components which make it possible to verify or compare the sequence and/or the size of the amplified fragment.

Indeed, in the context of the present invention, depending on the pair of primers used, it is possible to obtain very different results. Thus, the use of primers which are internal to the deletion, are described in the present invention for RD4, RD5 and RD8, is such that no amplification product is detectable in *M. bovis* BCG. However, the use of primers external to the region of deletion does not necessarily give the same result, as regards for example the size of the amplified fragment, depending on the size of the deleted region in *M. bovis* BCG. Thus, the use of the pair of primers SEQ ID No. 5/SEQ ID No. 6 for the detection of RD6 is likely to give rise to an amplicon in *M. bovis* BCG of about 3 801 bp whereas the use of the pair of primers SEQ ID No. 11/SEQ ID No. 12 for the detection of RD9 will give rise in *M. bovis* BCG to an amplicon of about 1 018 bp.

The subject of the invention is also the use of at least one pair of primers as defined above for the amplification of DNA sequences of *M. bovis* BCG/*M. bovis* or *M. tuberculosis*.

The benefit of the use of several pairs of primers will be quite obviously to cross the results obtained with each of them in order to refine the result of the analysis. Indeed, when it is indicated, in the context of the present invention, that some deletions are specific to *M. bovis* BCG/*M. bovis*, that is not completely accurate since some of them are also found in *M. microti* OV254, in *M. tuberculosis* CSU#93 and in *M. africanum* as well as certain clinical isolates (table 2). Thus, the use of the pair of primers SEQ ID No. 1/SEQ ID No. 2 specific for the RD4 region will not give rise to amplicons of normal size with *M. bovis* BCG/*M. bovis* in the biological sample. On the other hand, if the pair of primers used is SEQ ID No. 5/SEQ ID No. 6 specific for RD6 and that amplicons of normal size are not found, it will not be possible, from this result only, to discriminate between the presence, in the biological sample, of *M. bovis* BCG/*M. bovis, M. microti* OV254 and *M. tuberculosis* CSU#93.

The discrimination will be more radical when it will involve determining if the mycobacterium present in the biological sample to be analyzed is *M. bovis* BCG/*M. bovis* or *M. tuberculosis* H37Rv because the pairs of primers SEQ ID No. 15/SEQ ID No. 16 and SEQ ID No. 17/SEQ ID No. 18 are specific only for *M. tuberculosis* H37Rv. Consequently, the absence of amplicon of normal size during the use of either of these pairs of primers may be considered as indicative of the presence of *M. tuberculosis* H37Rv in the biological sample analyzed.

The subject of the present invention is also the products of expression of all or part of the nucleotide sequences deleted from the genome of. *M. bovis* BCG/*M. bovis* and present in *M. tuberculosis* or conversely as listed in table 1.

The expression "product of expression" is understood to mean any protein, polypeptide or polypeptide fragment resulting from the expression of all or part of the abovementioned nucleotide sequences and preferably exhibiting on least one of the following characteristics:

capacity to export or secrete by a mycobacterium and or be induced or repressed during infection with mycobacterium, and/or capacity to induce, repress or modulate directly or indirectly a mycobacterial virulence factor, and/or capacity to induce an immunogenicity reaction directed against a mycobacterium, and/or capacity to be recognized by an antibody specific for a mycobacterium.

Indeed, the subject of the present invention is also a method for the discriminatory detection in vitro of antibodies directed against *M. bovis* BCG/*M. bovis* or *M. tuberculosis* in a biological sample, comprising the following steps:

a) bringing the biological sample into contact with at least one product of expression as defined above, b) detecting of the antigen-antibody complex formed.

The subject of the invention is also a method for the discriminatory detection of a vaccination with *M. bovis* BCG or an infection by *M. tuberculosis* in a mammal, comprising the following steps:

a) preparation of a biological sample containing cells, more particularly cells of the immune system of said mammal and more particularly still F cells, b) incubation of the biological sample of step a) with at least one product of expression in accordance with the present invention, c) detection of a cellular reaction indicating prior sensitization of the mammal to said product, in particular cell proliferation and/or synthesis of proteins such as gamma-interferon.

Cell proliferation may be measured, for example, by incorporating $^3$H-Thymidine.

The invention also relates to a kit for the in vitro diagnosis of an *M. tuberculosis* infection in a mammal optionally vaccinated beforehand with *M. bovis* BCG comprising:

a) a product of expression in accordance with the present invention, b) where appropriate, the reagents for the constitution of the medium suitable for the immunological reaction, c) the reagents allowing the detection of the antigen-antibody complexes produced by the immunological reaction, d) where appropriate, a reference biological sample (negative control) free of antibodies recognized by said product, e) where appropriate, a reference biological sample (positive control) containing a predetermined quantity of antibodies recognized by said product.

The reagents allowing the detection of the antigen-antibody complexes may carry a marker or may be capable of being recognized in turn by a labeled reagent, more particularly in the case where the antibody used is not labeled.

The subject of the invention is also mono- or polyclonal antibodies, their chimeric fragments or antibodies, capable of specifically recognizing a product of expression in accordance with the present invention.

The present invention therefore also relates to a method for the discriminatory detection of the presence of an antigen of *M. bovis* BCG/*M. bovis* or *M. tuberculosis* in a biological sample comprising the following steps:

a) bringing the biological sample into contact with an antibody in accordance with the invention, b) detecting the antigen-antibody complex formed.

The invention also relates to the kit for the discriminatory detection of the presence of an antigen of *M. bovis* BCG/*M. bovis* or *M. tuberculosis* in a biological sample comprising the following steps:

a) an antibody in accordance with the invention, b) the reagents for constituting the medium suitable for the immunological reaction, c) the reagents allowing the detection of the antigen-antibody complexes produced by the immunological reaction.

The abovementioned reagents are well known to a person skilled in the art who will have no difficulty adapting them to the context of the present invention.

The subject of the invention is also an immunological composition, characterized in that it comprises at least one product of expression in accordance with the invention.

Advantageously, the immunological composition in accordance with the invention enters into the composition of a vaccine when it is provided in combination with a pharmaceutically acceptable vehicle and optionally with one or more immunity adjuvant(s) such as alum or a representative of the family of muramylpeptides or incomplete Freund's adjuvant.

The invention also relates to a vaccine comprising at least one product of expression in accordance with the invention in combination with a pharmaceutically compatible vehicle and, where appropriate, one or more appropriate immunity adjuvant(s).

Standard knowledge on the evolution of the *M. tuberculosis* complex is based on the hypothesis that *M. tuberculosis* is derived from *M. bovis* (Sreevatsan et al., 1997). However, a distribution of RD1 to RD10 among the tuberculous complex suggests that a linear evolution of *M. tuberculosis* from *M. bovis* is too simplistic. It appears, indeed, in a more probable manner, that the two bacilli are derived from a common strain, that the deletions therefore reflect the adaptation of the bacilli to their particular niche, that is to say that the loss of RD4 to RD10 probably helped *M. bovis* to become a more potent pathogenic agent for bovines than *M. tuberculosis*. Functional genomic studies will determine which role these deletions play in the phenotypic differentiation of the tuberculous complex.

Finally, the inventors have detected, still by comparing the BAC of *M. tuberculosis* H37Rv and the BAC of *M. bovis* BCG, two duplications in the genome of *M. bovis* BCG-Pasteur, called DU1 and DU2. They are duplications of regions of several tens of kilobases which appear to be absent both from the *M. bovis* and *M. tuberculosis* H37Rv type strain. The detection of these two duplications was made following digestion of the same clones for each BAC with HindIII and analysis on a pulsed-filled electrophoresis gel (PFGE). These observations have been confirmed by hybridization of the digested chromosomal DNA derived from *M. bovis* BCG, from the type strain of *M. bovis* and *M. tuberculosis* H37Rv with selected probes covering the duplicated regions. Primers specific for the rearranged regions were prepared and tested on the genomic DNA from additional isolates of *M. bovis* BCG and *M. tuberculosis.*

It was determined that DU1 and DU2 were present in three strains of *M. bovis* BCG including in *M. bovis* BCG-Pasteur and absent from three other substrains of *M. bovis* BCG.

These two duplications are also absent from the type strain of *M. bovis* and *M. tuberculosis* H37Rv.

Thus, still in the context of the present invention in relation to the discriminatory detection of *M. bovis* or *M. tuberculosis*, the subject of the invention is also a method for the discriminatory detection and identification of *M. bovis* BCG or *M. tuberculosis* in a biological sample comprising the following steps:

- digestion, with a restriction enzyme, of at least part of the genome of the mycobacterium present in a biological sample to be analyzed, and
- analysis of the restriction fragments thus obtained.

The digestion with the restriction enzyme may indeed be carried out either on the entire genome of the mycobacterium, or on one or more clones of the library produced from the genome in question.

Preferably, the restriction enzyme used in the context of the abovementioned method is HindIII.

As regards the analysis of restriction fragments, it may consist in counting said fragments and/or in determining their length. Indeed, as is explained below, HindIII digestion of *M. bovis* BCG gives rise to one fragment more than those obtained after HindiIII digestion of the genome of *M. tuberculosis* H37Rv. The number of fragments thus obtained may also be complemented by the determination of their length. This may be carried out by means of techniques well known to persons skilled in the art, for example on a pulsed filled electrophoresis gel (PFGE). It has thus been possible to determine that the additional fragment appearing after HindIII digestion of the genome of *M. bovis* BCG-Pasteur had a size of about 29 kb.

Another way of analyzing the restriction fragments resulting from the enzymatic digestion of the genome of the mycobacterium as described above consists in bringing said fragments into contact with at least one appropriate probe, covering for example the duplicated region, under hybridization conditions so as to then identify the number and size of the fragments which have hybridized. The probes used for this purpose may be labeled or nonlabeled according to techniques well known to persons skilled in the art.

Thus, the probe may be obtained by amplification of the genomic DNA with primers chosen from the group SEQ ID No. 31, SEQ ID No. 32, SEQ ID No. 33 or SEQ ID No. 34 with the pair:

- SEQ ID No. 31/SEQ ID No. 32 specific for DU1
- SEQ ID No. 33/SEQ ID No. 34 specific for DU2

It is also possible to analyze the fragments by carrying out amplification of the fragments obtained with primers chosen from the group SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27 and SEQ ID No. 28 with:

- SEQ ID No. 19, SEQ ID No. 20/SEQ ID No. 21 specific for JDU1
- SEQ ID No. 22, SEQ ID No. 24/SEQ ID No. 23, SEQ ID No. 25 specific for JDU2A
- SEQ ID No. 26/SEQ ID No. 27, SEQ ID No. 28 specific for JDU2B It is also possible to amplify the fragments obtained with primers chosen from the group SEQ ID No. 35, SEQ ID No. 36, SEQ ID No. 37 and SEQ ID No. 38 specific for DU1 and then to analyze them by sequencing.

LEGEND TO THE FIGURES

FIGS. 1A to 1D: Map of the BAC of *Mycobacterium bovis* BCG-Pasteur superposed on the BAC of *M. tuberculosis* H37Rv and on the cosmid maps (these figures should be read from left to right and from top to bottom, FIG. 1A at the top left, FIG. 1B at the top right, FIG. 1C at the bottom left and FIG. 1D at the bottom right).

The "X" clones correspond to the clones in pBeloBAC11 of *M. bovis* BCG, the "XE" clones correspond to the clones in pBACe3.6 of *M. bovis* BCG, the "Rv" clones correspond to the clones in pBeloBAC11 of *M. tuberculosis*, the clones "Y" correspond to the clones in the cosmid pYUB328 of *M. tuberculosis* and the "I" clones correspond to the clones in the cosmid pYUB412 of *M. tuberculosis*. The location of each deletion region is shown on the map. The scale bars indicate the position on the genome of *M. tuberculosis*.

FIGS. 2A to 2F: General view of the deleted regions RD5-RD10 (SEQ ID NOS: 39-50, respectivley in order of appearance).

The regions deleted from the genome of *M. tuberculosis* are delimited by arrows with a sequence flanking each deletion. The ORFs (open reading frames) are represented by "directed" boxes showing the direction of transcription as described above (Cole et al., 1998). The putative functions and the families of the ORFs are described in table 3. The stop codons are indicated by small vertical bars.

FIG. 3: Detection of the RD5 deletion.

Digestions of the Rv143 clone of the BAC with the endonucleases EcoRI, PstI and StuI revealed that fragments of 1.5 kb (EcoRI), 1.5 kb (PstI), 1.3 and 2.7 kb (StuI) show no binding with *M. bovis* or *M. bovis* BCG DNA probes (the absent bands are indicated by arrows). The size in kilobases (kb) is indicated on the left.

FIG. 4: The RvD1 and RvD2 regions

A. Size polymorphism in amplicons generated by flanking primers (i) RvD1 and (ii) RvD2. PCR reactions were carried out using the GeneAmp XL PCR kit (Perkin Elmer) with DNA templates of *M. tuberculosis* H37Rv, *M. bovis* and *M. bovis* BCG-Pasteur in combination with primers described in table 3. The size in kilobases is indicated on the left of each image.

B. Structure of the ORFs of the loci of RvD1 and RvD2. The sequence of the two loci was determined from *M. bovis* BCG Pasteur, the flanking sequence in *M. tuberculosis* H37Rv being shown. The putative functions of the ORFs are described in table 1 with vertical barriers representing the stop codons. SEQ ID NOS: 51-54, respectively in order of appearance from left to right.

Figure 5:
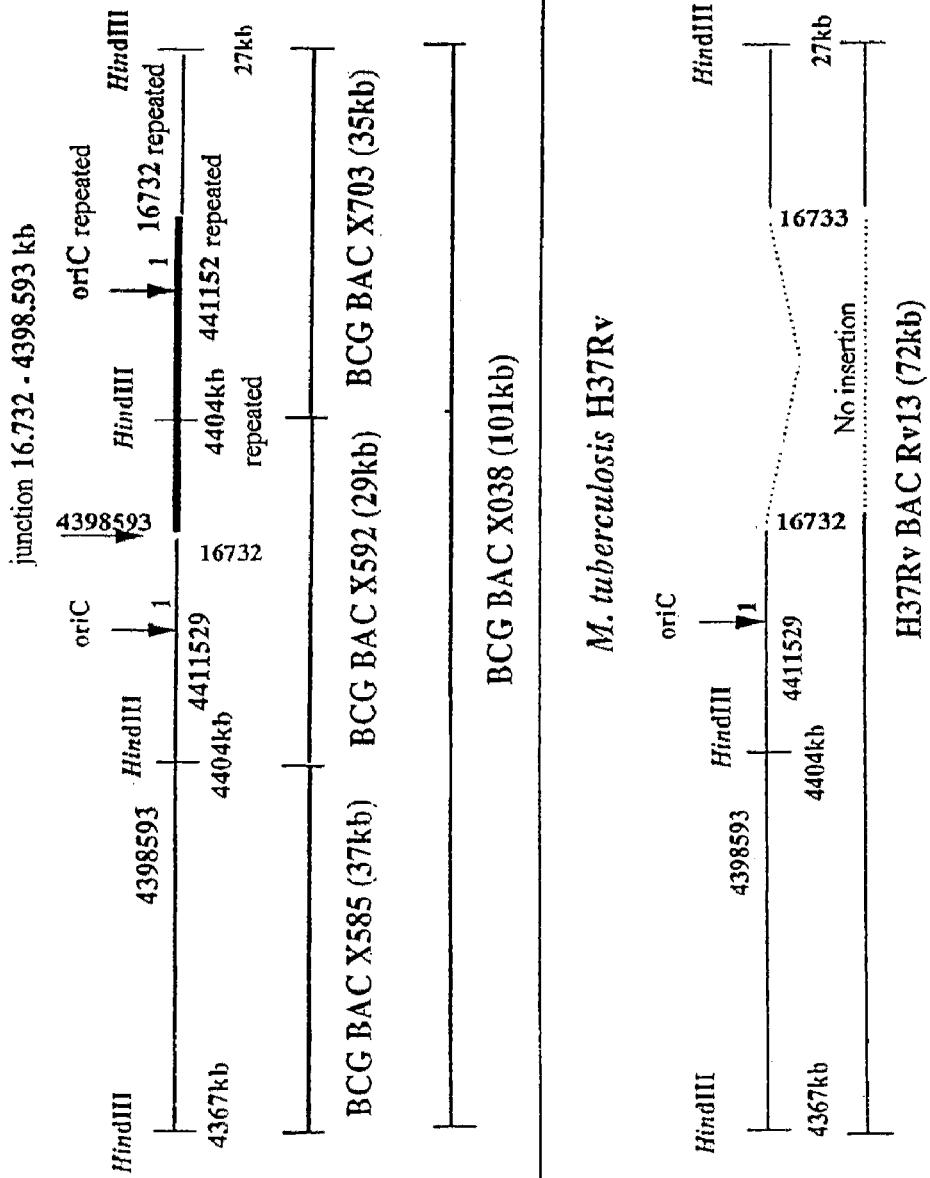

FIG. 5: Duplicated region DU1 in *M. bovis* BCG-Pasteur compared with the same region in *M. tuberculosis* H37Rv.

Figure 6:
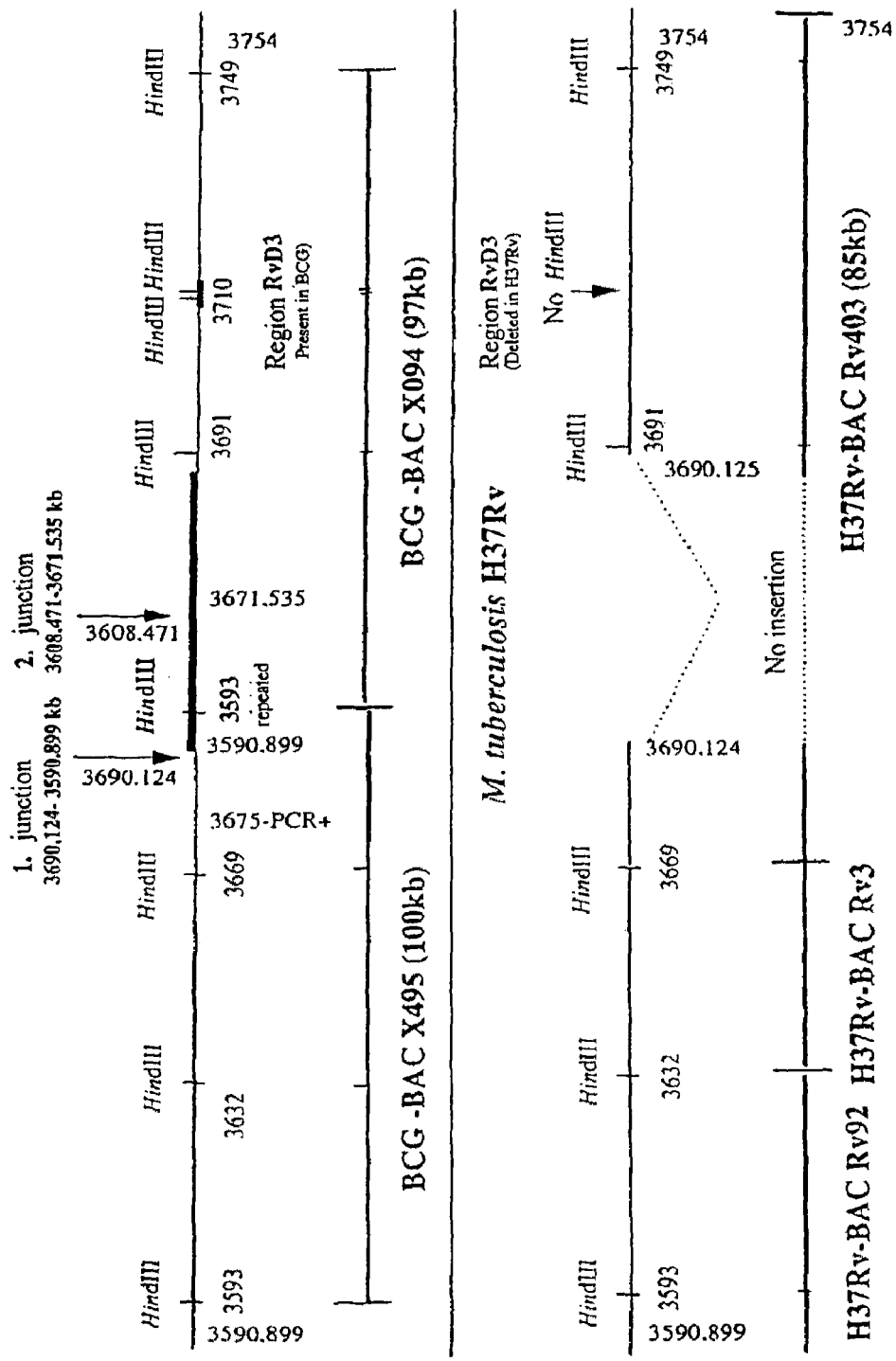

FIG. 6: Duplicated region DU2 in *M. bovis* BCG-Pasteur compared to the same region in *M. tuberculosis* H37Rv The present application is not limited to the above description and will be understood more clearly in the light of the examples below which should not in any manner be considered as limiting the present invention.

EXAMPLES

1. Procedures and Results

Construction of an *M. bovis* BCG-Pasteur BAC Library

Recent attempts for cloning very large inserts of mycobacterial DNA (120-180 kb) into the vector pBeloACll have resulted in failure (Brosch et al., 1998). To establish if this size determination was due to the vector pBeloBAC11, the inventors have tested in parallel the vector pBACe3.6 from BAC which uses the selection system sacB (Lawes and Maloy, 1995; Pelicic et al., 1996). Ligations carried out with fragments in the size ranges from 50 to 125 kb gave 5 to 10 times fewer transformants in pBACe3.6 than the control ligations using pBeloBAC11 (clones X). The size of an insert in the clones pBACe3.6 was approximately between the interval 40-100 kb, similar to what was observed for pBeloBAC11. This suggests that a size of about 120 kb is indeed the upper size limit for the feasibility of the cloning of mycobacterial DNA.

Definition of the Minimum Set of BCG BACs 100 clones randomly selected from pBeloBAC11 and pBACe3.6 libraries were sequenced at the ends to determine their position relative to the *M. tuberculosis* H37Rv chromosome (Cole et al., 1998). This gave a minimum network of clones on the genome but with a preferential group in the vicinity of the sole operon rrn, which was also observed during the construction of the *M. tuberculosis* BAC map (Brosch et al., 1998). To fill the holes between the positioned clones, PCR primers were prepared, on the basis of the sequence of the complete *M. tuberculosis* genome, so as to screen the BAC pools for specific clones. Using this methodology, clones covering more than 98% of the genome were isolated and positioned on the sequence of the *M. tuberculosis* genome.

A minimum set of 57 *M. bovis* BCG clones was necessary to cover the genome (FIG. 1). 56 of these clones are from the library pBeloBAC11 and 1 is from the library pBACe3.6, namely XE015 (at about 680 kb). Because previous experience had shown that the *M. tuberculosis* clones based on pBeloBAC11 exhibited exceptional stability (Brosch et al., 1998), these clones were preferred to the less characterized pBACe3.6 system. The clone XE015 represents a region for which the pBeloBAC11 clones could not be found. Two regions of about 36-52 kb, covered by no clone, are located at about 2 660 kb and about 2 960 kb on the genome. Previously, the isolation of cosmids and of *M. tuberculosis* BAC clones which covered the region at about 2 960 kb posed problems (Brosch et al., 1998) suggesting that this region could contain genes which are detrimental to *E. coli.*

Use of BAC Chips for Detecting Deletions in the *M. bovis* BCG Genome

This involves the detection, from the *M. tuberculosis* H37Rv BAC library, of 63 clones covering 97% of the genome (Brosch et al., 1998). Analysis in silico of the sequence of the *M. tuberculosis* genome revealed that the digestion of these clones with either PvuII or EcoRI gave rise to a reasonable number of restriction fragments for each clone. The digested fragments migrated through agarose gels, gave rise to spots on membranes and were then hybridized with the $^{32}P$-labeled genomic DNA of *M. bovis* BCG and *M. bovis*. The restriction fragments which did not hybridize with the DNA probes were considered to be absent from the genomes of *M. bovis* or BCG. As the initial screening used only two enzymes, it is possible that other deletions passed unnoticed. However, it is probable that all the important deletions (>5 kb) were detected by this approach.

From an analysis of the entire genome, 10 loci were identified which appeared to be absent from *M. bovis* BCG compared with *M. tuberculosis*. Hybridizations with the *M. bovis* genomic DNA revealed that 7 of these loci were also deleted in *M. bovis* compared with *M. tuberculosis*. Closer analysis revealed that the three deletions specific to *M. bovis* BCG were identical to the RD1-RD3 regions defined by the Stover team (Mahairas et al., 1996). Retaining the previous nomenclature, the 7 *M. bovis*/BCG deletions were designated RD4, RD5, RD6, RD7, RD8, RD9 and RD10 (FIGS. 1 and 2). Sequencing reactions using the corresponding BAC clones as template were used to define precisely the terminal regions of the deletions (FIG. 2, table 1).

RD4

RD4 is a 12.7 kb deletion previously characterized as a region absent from *M. bovis* and *M. bovis* BCG of the Pasteur, Glaxo and Denmark substrains (Brosch et al., 1998). Among the proteins encoded by the 110RFS, some show resemblance with the enzymes involved in the synthesis of the lipopolysaccharides. To determine if RD4 was deleted only in the bovine strains, *M. africanum, M. microti, M. tuberculosis* CSU#93 and 27 clinical isolates of *M. tuberculosis* were examined for the presence of the locus (table 2). PCR reactions using primers internal to RD4 (table 3) generated only products in non-bovine strains.

RD5

RD5 has a size of 8 964 bp located between the genomic positions 2626067-2635031 (FIG. 3, table 1). The region contained 8 ORFS (table 1), three of them: plcA, plcB and plcC, encode phospholipase C enzymes whereas two others encode proteins belonging to the ESAT-6 and QILSS families respectively (Cole et al., 1998; F. Tekaia, S. Gordon, T. Garnier, R. Brosch, B. G. Barrell and S. T. Cole, submitted). ORF Rv2352c encodes a PPE protein which is a member of the large family of proteins in *M. tuberculosis* (Cole et al., 1998). Another protein of the PPE family (Rv2352c) is truncated in *M. bovis* BCG because of the fact that one of the deletions of the terminal parts is situated in the ORF. Searches in databases revealed that a segment of 3 013 bp of RD5 was virtually identical to the mpt40 locus previously described, shown by Pattaroyo et al. to be absent in *M. bovis* and *M. bovis* BCG (Leao et al., 1995). Primers intended to amplify the internal part of RD5 (table 3) were used in the PCR reactions with the DNA derived from various tubercle bacilli. No amplicon was produced from *M. bovis*, *M. bovis* BCG and *M. microti* templates (table 2), indicting that *M. micoti* also lacks a RD5 locus.

RD6

RD6 was mapped at the level of the insertion sequence IS1532, an IS element which is absent in *M. microti*, *M. bovis* and *M. bovis* BCG (Gordon et al., 1998) (table 1). The delimiting of the size of the deletion was complicated by the presence of repeat regions directly flanking the IS element and requiring the use of primers outside the repeat region (table 3). These primers amplified the products in *M. bovis* and *M. bovis* BCG which are about 5 kb smaller than the *M. tuberculosis* amplicon. Primer walking was used to precisely locate the junctions of deletions and revealed a deletion of 4 928 b in *M. bovis* and *M. bovis* BCG (genomic position of *M. tuberculosis* 3846807-3841879). Like the 1S1532 element, it was determined that RD6 contained two genes encoding PPE proteins (Rv3425 and Rv3426) and part of Rv3424c whose function is unknown (table 1).

RD7

The RD2 deletion described in Mahairas et al. (Mahairas et al., 1996) was mapped in the *M. tuberculosis* Rv420 clone and the results obtained by the inventors have suggested the existence of an additional deletion in *M. bovis* BCG which is very close to RD2. Hybridizations were repeated using the *M. bovis* genomic DNA as probe since this strain contains RD2 sequences, thus simplifying the identification of other deleted fragments. This analysis (FIG. 2) revealed a 12 718 bp deletion in *M. bovis* BCG compared with *M. tuberculosis*, located 336 bp upstream of RD2, at positions 2208003-2220721 on the *M. tuberculosis* genome. The RD7 region contains 14 ORFs (table 3). 8 of them (Rv1964-1971) constitutes part of the operon with the putative invasine gene mce3 (Cole et al., 1998). The ORFs Rv1968, Rv1969, Rv1971, Rv1973 and Rv1975 could encode possible proteins exported or expressed at the surface since they contain putative N-terminal signal sequences or membrane anchoring. They are all members of the Mce family and have common properties (Tekaia et al., submitted). Interestingly, Mce3 and Rv1968 contain the tripeptide "RGD" or Arg-Gly-Asp, a motif involved in cellular attachment (Ohno, 1995; Relman et al., 1989). Rv1977, which is truncated by RD7, encodes a protein exhibiting similarities (38.5% identity over 275 amino acids) with a hypothetical polypeptide and the PCC 6 803 strain of *Synechocystis*. PCR analysis (table 2) revealed that RD7 was present in 30 clinical isolates of *M. tuberculosis* as well as in *M. africanum* and *M. tuberculosis* CSU#93. The locus was however absent from *M. microti*, *M. bovis* and *M. bovis* BCG.

RD8

RD8 covers a region of 5 895 bp positions on the genomic sequence of *M. tuberulosis* at 4556836-4062731. The deletion contains 6 ORFs (FIG. 2, table 1) with a seventh ORF: lpqQ which encodes lipoprotein truncated at its 5' end by the deletion. Among these 6 ORFs, Rv3619c and Rv3620c encode members of the ESAT-6 and QILSS families (Cole et al. 1998, Harboe et al., 1996; F. Tekaia, et al., submitted) and two other ORFs encode PE and PPE proteins. The other 2 ORFs, ephA and Rv3618, encode a putative epoxide hydrolase and a monooxygenase respectively. PCR analysis directed against an internal segment of RD8 (table 2) revealed that the region was also deleted in the *M. bovis* and *M. microti* wild type.

RD9 and RD10

The 2 030 bp deletion spanned by RD9 covers 2 ORFs, Rv2037c and Rv2074, which probably encode an oxidoreductase and an unknown protein respectively (table 1). 2 additional ORFs are truncated by RD9: Rv2075c encodes a putative exported protein whereas cobL encodes a precorrin methyltransferase involved in the synthesis of cobalamin. PCR analysis with flanking primers (table 3) revealed that RD9 is also present in *M. africanum* and *M. microti* (table 2). RD10 is a 1 903 bp deletion which truncates 2 ORFs, echA1 and Rv0223, which encode an enoyl-CoA hydratase and an aldehyde dehydrogenase respectively (table 1). PCR reactions revealed that RD10 was absent from *M. microti* as well as from *M. bovis* and BCG.

Other Differences Between *M. tuberculosis* and BCG

Figure 4A:
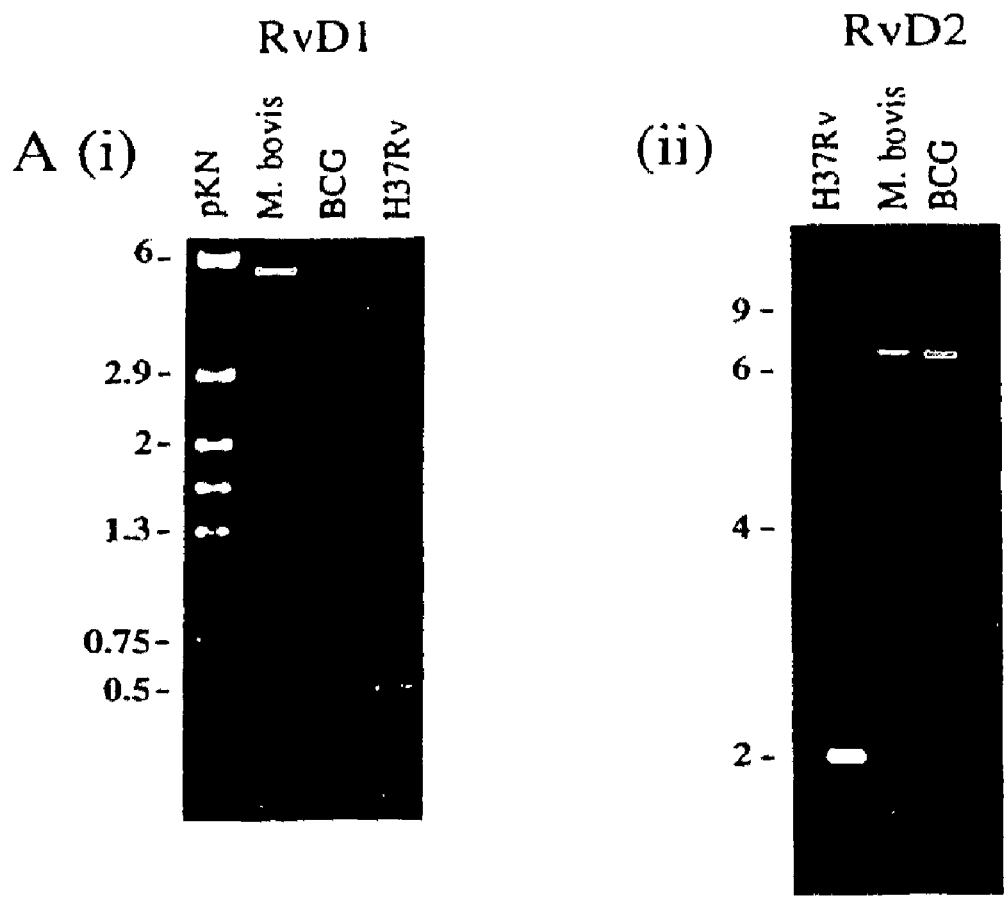

Given the fact that the genomes of tubercle bacilli are highly conserved (Sreevatsan et al., 1997), direct local comparison may be undertaken in a simple and targeted manner by examining the restriction enzyme profiles generated from *M. tuberculosis* and *M. bovis* BCG BAC clones which cover the same regions. Comparative mapping of the region covered by the clone X318 has identified this region as being very different from the corresponding *M. tuberculosis* clones. The data relating to the terminal sequences from the clone X066 revealed that if its terminal sequence SP6 made it possible to position about 2 380 kb on the *M. tuberculosis* template, the terminal sequence T7 would not generate any significant similarity with any sequence of H37Rv, indicating that one end of X066 was internal to the DNA segment present in BCG but absent from H37Rv. Sequencing primers were used to walk along the BCG BAC clone X318 (FIG. 1) and revealed the insertion at the 2238724 bp position in the *M. tuberculosis* genome. Used in PCR reactions, the *M. bovis* BCG and *M. bovis* templates generated larger amplicons of about 5 kb than the product of *M. tuberculosis* H37Rv (FIG. 4A). The whole insert, designated RvD1, was sequenced from X318 BCG. The insert of 5 014 bp extended the *M. tuberculosis* Rv2024c ORF by 2.8 kb and contained an additional ORF, RvD1-ORF2, of 954 bp (table 1, FIG. 4B). RvD1-ORF1 can be superposed over the 5' joining point of the deletion and extends inside the flanking DNA. FASTA analysis revealed that RvD1-ORF1 and ORF2 encode proteins exhibiting no significant similarity with other proteins in databases. Extended Rv2024c showed certain similarities (36.5% identity of 946 amino acids) with a *Helicobacter pylori* hypothetic protein (accession No. 025380). The loss of this sequence clearly had no consequence on the virulence of *M. tuberculosis* H37Rv since this strain is fully virulent in animal models. PCR analysis specific for the locus demonstrated its presence in several but not in all the clinical isolates and in all the BCG strains tested (table 2).

Figure 4B:
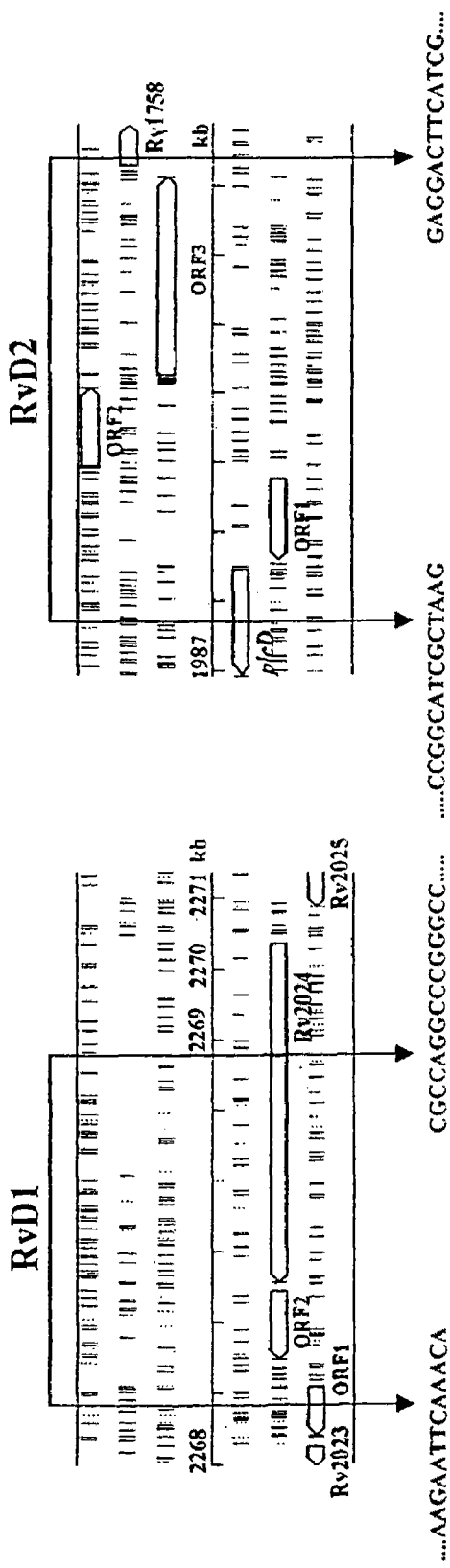

An ORF encoding a phospholipase, plcD, is interrupted by IS6110 in *M. tuberculosis* H37Rv (Cole et al., 1998). To determine if plcD was intact in other members of the tuberculous complex, primers flanking the insertion site IS6110 (table 3) were used in PCR reactions with *M. bovis*, *M. bovis* BCG and *M. tuberculosis* H37Rv. This revealed polymorphism at the locus plcD where the *M. bovis* and *M. bovis* BCG amplicons were about 5 kb larger than the product of H37Rv (FIG. 4A). This deletion of about 5 kb in the *M. tuberculosis* H37Rv genome compared with *M. bovis* BCG was called RvD2. The sequencing of the *M. bovis* BCG BAC clone X086 revealed that RvD2 was positioned between bases 1987699-19890045 in the *M. tuberculosis* genome. The region comprises 6.5 kb and contains 3 ORFs encoding an unknown protein, an oxidoreductase and a membrane protein, and it extends the plcD gene in order to encode a product of 514 amino acids (FIG. 4B, table 1).

II. EXPERIMENTAL DATA

Bacterial Strains and Plasmids

The strains of the *M. tuberculosis* complex (*Mycobacterium africanum*, *Mycobacterium microti*, *Mycobacterium tuberculosis*, *Mycobacterium bovis* and *Mycobacterium bovis* BCG) and substrains of *M. bovis* BCG (Danemark, Glaxo, Russe, Japonais, Pasteur and Moreau) were obtained from laboratory stalks (Unite de G. M. B., Institut Pasteur). *Mycobacterium tuberculosis* CSU#93 was received from John BELISLE, Department of Microbiology, Colorado State University, Fort Collins, Colo. 80523. Non-epidemic clinical isolates of *M. tuberculosis* were provided by Beate HEYM, Ambroise Paré hospital, 9 avenue Charles de Gaulle, 92104 BOULOGNE CEDEX, FRANCE. The BAC vectors pBeloBAC11 (Kim et al., 1996) and PBACe3.6 (Genbank accession No. U80929) were given by H. SHIZUYA, Department of Biology, California Institute of Technology, Pasadena, Calif., and P. de JONG, Roswell Park Cancer Institute, Human Genetics Department, Buffalo, N.Y., respectively. The vectors and the derived recombinants were maintained in *E. coli* DH10B.

Preparation of the Genomic DNA

The preparation of the genomic DNA in agarose cubes from *M. Bovis* BCG Pasteur was carried out as previously indicated (Philipp et al., 1996; Philipp et al., 1996) but with two proteinase K digestions for 24 h each, rather than one digestion of 48 h. The cubes were stored in 0.2 M EDTA at 4° C. and washed twice in 50 ml of Tris-EDTA (pH 8)/Triton X-100 (0.1%) at 4° C. for 1 h, and then washed twice in 50 ml of a buffer of restriction enzyme Triton X-100 (0.1%) for 1 h at room temperature before use.

Construction of the BAC library

A DNA vector was prepared as previously indicated (Woo et al., 1994). Partial HindIII and EcoRI digestions of the DNA in agarose, for cloning into pBeloBAC11 and pBACe3.6 respectively, and then contour-clamped homogeneous electric field (CHEF) migration were carried out as previously described (Brosch et al., 1998). 5 zones, 50-75 kb, 75-100 kb, 100-125 kb and 150-170 kb were excized from agarose gels and stored in TE at 4° C. Ligations with the vectors pBeloBAC11 and pBACe3.6 and transformation in *E. coli* DH10B were carried out as previously described (Brosch et al., 1998). The pBeloBAC11 transformants were selected on LB agar containing 12.5 μg/ml of chloramphenicol, 50 μg/ml of X-gal and 25 μg/ml of IPTG, and were screened with white recombinant colonies. The pBACe3.6 transformants were selected on LB agar containing 12.5 μg of chloramphenicol and 5% of sucrose. The recombinant clones were subcultured, in duplicates, in 96-well microtiter plates containing a 2xYT medium with 12.5 μg of chloramphenicol and were incubated overnight at 37° C. An equal volume of glycerol at 80% was then added to the wells and a plate was stored at −80° C. as master plate. The remaining plate was used to make sets of clones for screening purposes (see above).

Preparation of DNA from Recombinants and Examination of the Size of the Inserts

A recombinant carrying a DNA plasmid was prepared from 40 ml of culture and was grown on the 2xYT medium containing 12.5 μg of chloramphenicol as previously described (Brosch et al., 1998). 100-200 ng of DNA were digested with DraI (Gibco-BRL) and the restriction products were separated on a pulsed-field electrophoresis gel (PFGE) with an LKB-Pharmacia CHEF apparatus using a 1% (weight/volume) and a pulse of 4 seconds for 15 h at 6.25 V/cm. PFGE markers of average low size (New England Biolabs) were used as size standard. The sizes of the inserts were estimated after ethidium bromide staining and visualization with UV light.

Sequencing Reactions

Sequencing reactions were carried out as previously indicated (Brosch et al., 1998). For clones isolated from the pBeloBAC11 library, the primers SP6 and T7 were used to sequence the ends of the inserts whereas for the clones pBACe3.6, the primers derived from the vector were used. The reactions were loaded onto 6% polyacrylamide gels and electrophoresis was carried out with a 373A or 377 automated DNA sequencer (Applied Biosystems) for 10 to 12 h. The reactions generally gave between 300 and 600 bp of readable sequences.

BAC Chips

The overlapping clones from the pBeloBAC11 library of *M. tuberculosis* H37Rv (Brosh et al., 1998) were selected so that 97% of the *M. tuberculosis* genome was represented. The DNA prepared from these clones was digested with EcoRI (Gibco-BRL) or PvuII (Gibco-BRL) and was run on 0.8% agarose gels 25 cm in length, at a low voltage for 12 to 16 h. After staining and visualization under UV, the agarose gels were treated by the standard Southern method and the DNAs were transferred onto Hybond-C Extra nitrocellulose membranes (Amersham). The DNA was fixed on the membrane by heating at 80° C. for 2 h. The genomic DNA of *M. tuberculosis* H37Rv, *Mycobacterium bovis* ATCC 19210 and *M. bovis* BCG Pasteur was labeled with [$\alpha$-$^{33}$P]dCTP using the Prime-It II kit (Stratagene). The probes were purified on a P10 column (Biorad) before use. Hybridizations were carried out as previously described (Philipp et al., 1996). The purified labeled probes were dissolved in a 5×SSC solution (1×SSC is 0.5 M sodium chloride; 0.015 M sodium citrate), and 50% (weight/volume) formamide. The hybridization was carried out at 37° C., and the membranes were washed for 15 min at room temperature in 2×SSC/0.1% SDS and then in 1×SSC/0.1% SDS and finally in 0.1×SSC/0.1% SDS. The results were interpreted from autoradiograms. In general, it was difficult to visualize on the autoradiograms the fragments of less than 1 kb, especially after repeated use of the membranes. The fragments larger than 1 kb gave clearer results. The clones which appeared to contain fragments with no counterpart in *M. bovis* BCG were subcultured for subsequent analyses. The genomic sequence allowed the establishment of restriction maps with the aim of determining the suspected regions of deletion, making it possible to select enzymes giving the best resolution of the regions. Clones could thus be digested with a second range of enzymes (generally PstI and StuI, with EcoRI included as a control) and hybridized in order to obtain a more accurate size of the deletion. The sequencing primers flanking the deletions were thus designated and used in the sequencing reactions with the corresponding BAC of *M. bovis* BCG used as template.

PCR Analysis

The primers used in the PCR reactions are listed in tables 3 and 4. The reactions for expected products of less than 3 kb were carried out with a standard Taq polymerase (Boehringer Mannheim). The reactions used 5 μl of 10×PCR buffer (100 mM (3-mercaptoethanol, 600 mM Tris-HCl, pH 8.8), 20 mM $MgCl_2$, 170 mM $(NH_4)_2SO_4$, 5 μl of nucleotide mixture at 20 mM, 0.2 μM of each primer, 10-50 ng of DNA template, DMSO at 10%, 0.5 unit of Tag polymerase and sterile distilled water to 50 μl. The heat cycles were carried out with a PTC-100 amplifier (MJ Inc.) with an initial denaturation step of 90 seconds at 95° C. followed by 35 cycles of 30 seconds at 95° C., 1 min at 55° C. and 2 min at 72° C.

The PCR reactions capable of giving rise to products greater than 3 kb were carried out using the PCR GeneAmp XL kit (Perkin Elmer). The reactions were initiated according to the manufacturer's instructions, with 0.8 mM Mg(OAc)$_2$, 0.2 µM of each primer and 10-30 ng of DNA template per reaction. The heat cycles were carried out at 96° C. for 1 min, then followed by 15 cycles in 2 stages at 94° C. for 15 seconds and 70° C. for 7 min, followed by 20 cycles in 2 stages at 94° C. for 15 seconds and 70° C. for 8 min plus 15 seconds per cycle.

Computer Analysis

The data relating to the sequences were transferred from the automated ABI373A sequencer to the Sun or Digital work station and edited using the TED software from the Staden package. The edited sequences were compared with the inventors' database relating to *M. tuberculosis* (H37Rv.dbs) to determine the relative positions of the terminal sequences on the sequence of the *M. tuberculosis* genome. With this method, a map of the *M. bovis* BCG BAC clones was constructed using the *M. tuberculosis* H37Rv sequence as template.

To make the genomic comparison, digestions in silico using restriction enzymes were carried out with the NIP (Nucleotide Interpretation Program) software using the Staden package. The Display and Analysis program (DIANA) of the Sanger Centre, Cambridge, UK, was used to interpret the sequence data.

Accession Numbers for the DNA Sequences

The nucleotide sequences which flank each RD locus in *M. bovis* BCG have been deposited in the EMBL database. The accession numbers for RD5, RD6, RD7, RD8, RD9 and RD10 are AJ007300, AJ131209, AJ007301, AJ131210, Y181604 Y18604 and AJ132559, respectively. The sequences of RvD1 and RvD2 in *M. bovis* BCG have been deposited under the Nos. Y18605 and U18606 respectively.

Detection of the Duplicated Region DU1

DU1 was the first depleted region observed when the bands for HindIII digestion of the clone X038 of the BCG BAC and of the clone Rv13 of the H37RvBAC were compared. The two clones X038 and Rv13 had identical terminal sequences, extending from position HindIII ~4 367 kb to the HindIII site ~0 027 kb (via 4411529 b) on the sequence of the genome of *M. tuberculosis* H37Rv (MTBH37RV), spanning the replication origin.

Analysis in silico of the HindIII restriction sites for the region given between ~4 367 kb and ~0 027 kb revealed a HindIII site at position ~4 404 kb. Consequently, digestion of these clones should show two restriction fragments plus the band specific for the vector at about 8 kb. That was the case for the H37Rv Rv13 clone. By contrast, the clone X038 of the BCG BAC showed three bands plus the band specific for the vector at about 8 kb, two of them were identical to the Rv13 scheme. The additional band has a size of about 29 kb. Additional PFGE analyses using DraI revealed that X038 is indeed 29 kb longer than Rv13. For PCR screening of the BCG BAC pools using selected oligonucleotides, the inventors were able to identify three further clones X covering the parts of this genomic region in BCG: X585, X592, X703. The terminal sequence and the PFGE analysis showed that each of these clones contains an insert of a different size, corresponding to the three bands observed in the results of digestion of X038 (FIG. 5).

The terminal sequences are: X585 (~4 367-4 404 kb); X592 (~4 404-4404 kb); X703 (~4 404-0 027 kb). The sequences were repeated twice with the same results. The strange result according to which the clone X592 has T7 and SP6 and in the same genomic region could be explained by duplication of this genomic region in BCG and also give information on the extent of the rearrangement. Additional comparative restriction analyses of the clones X585, X592, X703 and X038 with EcoRI revealed that X592 and X703 have the same restriction pattern with the exception of a 10 kb band present in X703 but absent from X592. On the basis of these results, primers were prepared for the amplification of the joining region where the duplicated DNA segment joins the unique region.

PCR analysis with primers at 16.000 and at 4398.700 bp (SEQ ID No. 19 and 21) gave a product of an expected size from the clone X592 and also on the BCG-Pasteur genomic DNA. Sequencing of the PCR products obtained directly on the BAC DNA of the clone X592 revealed that the junction was indeed located at bases 16.732/4398.593 compared with the genomic sequence of H37Rv and that this genomic rearrangement resulted in the truncation of the Rv3910 and pknB genes. However, since this rearrangement is a tandem duplication, intact copies of the two genes could be present in the neighboring regions. PCR analysis with flanking primers of the Rv3920 and pknB genes confirmed this when the genomic DNA of BCG-Pasteur and of *M. tuberculosis* H37Rv were used. Additional proof of the rearrangement was obtained using a PCR fragment of 500 bp spanning the oriC region of H37Rv as $^{32}P$-labeled probe in order to hybridize the products of digestion of the genomic DNA of *M. tuberculosis, M. bovis* and *M. bovis* BCG-Pasteur under the stringent conditions previously described (Philipp et al., 1996). Whereas in *M. bovis* and *M. tuberculosis* a band having an average size of about 35 kb was detected, in *M. bovis* BCG-Pasteur two bands hybridized, one of approximately 35 kb and the other of 29 kb. In conclusion, DU1 corresponds to a tandem duplication of 29668 bp which results in merodiploidy for the sigM-pabA region (Rv3911-Rv0013).

PCR analysis using primers at 16.000 F (SEQ ID No. 19) or 16.500 F (SEQ ID No. 20) (sense primers) and at 4398.770R (SEQ ID No. 21) (reverse primer) on the genomic DNA of various BCG strains (Pasteur, Glaxo, Copenhagen, Russia, Prague, Japan) have revealed that products were only obtained from three strains, including *M. bovis* BCG-Pasteur. The other three substrates always gave negative results despite the confirmation of the positive controls.

As expected, the *M. bovis* and *M. tuberculosis* H37Rv type strains were also always negative. A summary of the mapping data is shown in FIG. 5.

The dnaA-dnaN region is generally regarded as the functional replication origin in mycobacteria since after insertion into plasmids whose own replication origin is absent, the capacity to autonomously replicate is restored. Since BCG-Pasteur is diploid for the dnaA-dnaN region, the inventors studied whether differences existed between the nucleotides of the two copies present on the two BAC X592 and X703 clones. Analysis of the BAC DNA sequence using primers of flanking and internal regions of the intergenic dnaA-dnaN region revealed no difference between the two copies of the minimal oriC region. Furthermore, these sequences were identical to those disclosed in the literature for this BCG strain. This study suggests that the two copies of oriC ought to be functional.

Detection of the Duplicated Region DU2

The second big genomic rearrangement observed in the *M. bovis* BCG-Pasteur chromosome was found by analyzing several BCG BAC clones covering a genomic region of about 200 kb (3 550-3 750 kb). Their sizes, evaluated by PFGE, did not conform to those expected from the H37Rv genome and data relating to the terminal sequences. Direct comparisons were complicated by the presence of an IS6110 element in this region of the *M. tuberculosis* H37Rv chromosome which led to a small RvD5 deletion.

The terminal sequences of BAC X495 were both located around the HindIII site at 3 594 kb, whereas the PFGE results showed that the clone has a size of about 106 kb, containing three HindIII fragments, of about 37.5 kb, about 37 kb and about 24 kb in addition to the vector. The 24 kb band was about 2 kb longer than the fragment corresponding to HindIII of 22 kb in Rv403. This observation led to the hypothesis that the genomic region at around 3 594 kb must have been duplicated, giving rise to the introduction of a novel HindIII site at the point where the clone X495 ends. To show this, several primers in the chromosomal region of 3 589 kb to 3 594 kb were tested for the sequencing of the BAC X495 DNA and a junction (JDU2A) was identified at bases 3690124/3590900 relative to the genomic sequence of H37Rv. This led to an interruption of the lpdA (Rv3303) gene but the PCR results indicated that an intact copy of this gene is present in the duplicated region.

Systematic analysis of other clones in the vicinity allowed the identification of 2 BACs independent of the BCG (X094 and X1026) which carried the same chromosomal fragment 3 594 to 3 749 kb. Although the terminal sequence data suggested that these clones had to have a size of about 155 kb, the size estimated by HindIII or DraI digestions followed by PFGE separation were only about 100 kb. This difference indicated that the inserts of clones X094 and X1026 probably extended from the repeated HindIII sites at 3 594 kb to the authentic HindIII site at position 3 749 kb, and that an internal deletion had taken place inside the duplicated unit.

This was confirmed by hybridization experiments under stringent conditions previously described on the genomic DNA, digested with HindIII, of *M. tuberculosis* H37Rv, *M. bovis* and BCG-Pasteur using the DNA of the radiolabeled X495 clone. The size of one of the bands which hybridized with this DNA in the HindIII profiles of *M. tuberculosis* H37Rv and *M. bovis* were about 22 kb, whereas the corresponding band in BCG was 24 kb exactly, which was observed with the BAC clones. Furthermore, the hybridization results showed that a band of 34 kb in the HindIII profile of the X094 clone also hybridized with the genomic DNA of the X495 clone, which confirmed that the X094 and X1026 clones contained the duplicated DNA of the genomic region covered by X495. PCR reactions and the sequence of the DNA of the X094 BAC clone allowed the identification of a second joining point JDU2B at an equivalent position at 3 608 471/3 671 535 in *M. tuberculosis* H37Rv. This confirmed that DU2 resulted from a direct duplication of a region of 99 225 bp corresponding to the sequences between positions 3 590 900 and 3 690 124 in the *M. tuberculosis* H37Rv genome, and an internal deletion of 63 064 bp then took place. The residual DU2 unit is thus 36 162 bp long, which is equivalent with the mapping data, and BCG-Pasteur is diploid for the Rv3213c-Rv3230c and Rv3290c-Rv3302c genes.

Finally, experiments involving PCR, PFGE mapping and sequencing of the terminal sequences with BAC X094 suggested that BCG-Pasteur contained additional DNA in the chromosomal region of the 3 691 to 3 749 kb HindIII site. Direct comparison with the *M. tuberculosis* Rv403 BAC clone allowed the detection of two additional HindIII sites in this region since the HindIII fragments of 48 kb present in Rv403 (corresponding to fragment 3 691 to 3 749) were represented by two bands of 22 to 36 kb in BCG. This region of the *M. tuberculosis* H37Rv chromosome contains a copy of IS6110 which is not flanked by the characteristic direct repeat units of 3 bp. It is now clear that there were initially two copies of IS6110 which served as substrate for a recombination event. This gave rise to the deletion of a segment of 4 kb of the genome of *M. tuberculosis* H37Rv (RvD5), which is always present in BCG, as well as in *M. bovis* and the clinical isolates of *M. tuberculosis*. Analysis of the sequence of this region indicated that this 4 kb fragment contains two HindIII sites and that there is absent therefrom the IS6110 sequence which is present at this site in *M. tuberculosis* H37Rv. Using internal primers for RvD5 (table 4), the inventors obtained amplicons with the genomic DNA of all the *M. bovis* BCG strains tested, and the *M. bovis* strain, as well as with the DNA of clones X094 and X1026, but not with the *M. tuberculosis* H37Rv and H37Ra strains.

Experiments with multiple sets of primers (3689.500 F (SEQ ID No. 22) or 3689.900 F (SEQ ID No. 24) (sense) 3591.000R (SEQ ID No. 23), 3591.500R (SEQ ID No. 25) or 3592.000R (reverse)) to amplify the joining region at the level of the base 3690124/3590900 (described above) in various *M. bovis* BCG strains revealed that amplicons could only be obtained from *M. bovis* BCG-Pasteur and from two other BCG substrates, whereas the other BCG substrates gave no amplicon. Confirmation of the results may be obtained on HindIII spots hybridized with labeled DNA derived from the 3689500E-3690.000R region which ought to give rise to bands with rearranged BCG strains, one of them has a size of about 24 kb, about 2 kb more than the corresponding band in the genomic digestions of *M. bovis* and *M. tuberculosis*. The second band of about 35 kb ought to be present only in the rearranged strains and not in *M. tuberculosis* H37Rv or the *M. bovis* type strain (FIG. 6).

The screening of clones of 2000× and XE (Gordon et al., 1999) for BACs containing both JDU2A and JDU2B junctions, that is to say which cover the complete rearranged region allowed the identification of three BACs (X1070, XE377 and XE256) which produced amplicons with the two sets of primers. The inserts were estimated by PFGE to have a size of 95, 86 and 97 kb respectively. On the basis of these PCR results, data corresponding to the terminal sequences and the presence of three chromosomal HindIII fragments of 37, 36 and 24 kb, the inventors concluded that the X1070 clone overlaps the X495 clone. However, it contained a chromosomal HindIII fragment of 36 kb which was neither present in the X495 clone nor in the X094 clone and, with the terminal sequence data, this would suggest the presence of a third copy of the HindIII site at 3 594 kb in the rearranged region. New proof of this was obtained when the XE256 and XE377 clones obtained from an EcoRI library in pBACe3.6 were analyzed. Depending on the terminal sequence data, XE256 extends from the EcoRI site at 3 597 kb to the EcoRI site at 3 713 kb, and XE377 from the EcoRI site at 3 679 kb to the EcoRI site at 3 715 kb. The fact that these clones repeatedly gave amplicons for the two cited joining regions JDU2A and JDU2B was not in agreement with their size and their terminal sequences. However, these data were coherent with the fact that the region of 36 162 bp of DU2 was present not only as one but rather as two tandem copies. Hybridization (according to the method of Philipp et al., 1996) of the fragments of HindIII digested DNA of the XE256, X1070 and XE377 clones with a 0.5 kb probe of the 3 675 kb genomic region confirmed the PCR results. A 24 kb fragment of the X1070 clone hybridized, equivalent to that of the X495 clone, and a single 36 kb fragment which corresponds to an additional copy of DU2 was also present. Two fragments of 33 and 34 kb of the XE256 clone hybridized with the probe. The 33 kb fragment corresponds to a region which extends from the HindIII site present in the vector adjacent to the EcoRI cloning site to the nearest HindIII site in the mycobacterial insert, whereas the 34 kb fragment is identical to that which is also present in the X094 clone. The 33 kb fragment partially overlapped the X1070 clone whereas the 34 kb HindIII fragment was identical to that present in the X094 and XE377 clones.

These data indicate that two tandem copies of DU2 exist in the BCG-Pasteur genome. This was confirmed by the hybridizations of the products of digestion with HindIII of the genomic DNA of BCG-Pasteur, M. tuberculosis H37Rv and M. bovis since all hybridized with the 3 675 probe. As expected, only one band of 22 kb was observed with M. tuberculosis and M. bovis whereas three bands of 24, 34 and 36 kb were detected, by hybridization, in the BCG-Pasteur genome. However, the hybridization signal for the 36 kb fragment was very weak. The fact that the 24 and 36 kb bands present in the BAC X1070 clone hybridized with the 3 675 probe with the same intensity, whereas those in the genomic DNA of BCG-Pasteur do not, suggests that only a subpopulation of the BCG-Pasteur culture contains the second copy of DU2. Thus, the difference observed in the intensity of hybridization may reflect that the second copy of DU2 was only recently acquired and indicates variants which contain one or two copy or copies of DU2 probably exist in the same M. bovis BCG-Pasteur culture.

Similar results were obtained with the genomic DNA fragments digested with XbaI from M. tuberculosis, M. bovis and BCG-Pasteur which hybridize with the 3 675 probe. In the M. tuberculosis H37Rv digestion, the 3 675 probe hybridized with a 183 kb fragment (genomic position 3 646 kb to 3 829 kb). The corresponding M. bovis fragment was approximately 178 kb, this difference in size being due to the absence of several insertion elements which are present only in the 183 kb M. tuberculosis H37Rv genomic fragment. The product of digestion with BCG-Pasteur XbaI contained two fragments of 215 and 250 kb which hybridized with the 3 675 probe. These two fragments corresponded to the 178 kb fragment observed in the M. bovis genome increased by or 72 kb because of the presence of one or two copies of DU2. It is of interest to note that the hybridization signal for the 250 kb fragment was less intense than the signal obtained for the 215 kb fragment, which confirms the previous observations with the products of digestion with HindIII.

These observations indicate that this region of the BCG genome is still dynamic and that a subpopulation of cells is triploid for the Rv3213c-Rv3230c and Rv3290c-Rv3302c genes. These comparative data between the sequence of the genome of M. tuberculosis H37Rv and of BCG-Pasteur indicate that BCG-Pasteur ought to be triploid for at least 58 genes, and that at one point of their evolution, their common ancestor contained duplicated copies of 60 additional genes which were lost when the deletion internal to DU2 occurred. Furthermore, the presence of DU1 and of DU2, and in particular the demonstration of the fact that DU2 is present in the form of two copies in a subpopulation of BCG-Pasteur, suggests that the tandem duplication process in BCG is still dynamic.

The invention therefore provides data which may make it possible to compare the various BCG strains with each other. Moreover, the invention shows the benefit of using mapping strategies with BACs as complement for sequencing the genome and allows the identification of possible drawbacks of projects which are based solely on the sequencing of clones by the "shot gun technique". Thus, without this BAC library, it is highly probable that these complex genomic rearrangements in the M. bovis BCG strains would not have been detected. It is therefore an advantage of the present invention to provide data which allow the characterization and possibly the immunogenic and protective classifications of the various BCG strains which are currently used clinically and for vaccine applications, and to provide information which allow the specific identification of M. tuberculosis in relation to M. bovis and M. bovis BCG, or information which allow the specific identification of M. bovis BCG in relation to M. bovis. The present invention thus provides important information for the study and the epidemiology of tuberculosis, and for the subsequent studies of genomic rearrangements in the different bacteria. The technique developed in the present invention is exemplified by the results of the present invention and may be applied to other bacterial and/or parasite genomes.

Thus, the fact that M. bovis BCG-Pasteur and two other substrains of M. bovis BCG have a duplicated complement set of genes responsible for major processes such as, inter alia, cell division and signal translation, comprising two replication origins, is one of the surprising aspects revealed to the inventors by this approach to genetic comparisons.

Since the biological material is subject to changes, and given that BCG vaccination trials highly varied protection results (0-80%), it could be important to evaluate if this variation in the efficacy of protection may be partly attributed to the choice of the BCG substrain used.

It is therefore advisable to carry out additional investigations in order to determine if a correlation exists between genomic features and phenotypic variations among the various BCG substrains.

The BAC libraries have been deposited at the Collection Nationale de Culture de Microorganismes (CNCM), 25 rue du Dr Roux, 75724 PARIS CEDEX 15, France according to the provisions of the Budapest treaty.

BAC of M. tuberculosis H37Rv Serial Number I1945
BAC of M. bovis BCG Serial Number I2049

TABLE 1

DESCRIPTION OF THE DELETIONS

| DELE-TIONS | ORF/GENE | POSITION ® ON THE GENOME OF M. TUBERCULOSIS H37RV | SIZE OF THE PRODUCT | PUTATIVE FUNCTION OR FAMILY |
|---|---|---|---|---|
| RD5 | Rv2346c | 2625889-2626170 | 94 aa | ESAT-6 family |
| | Rv2347c | 2626224-2626517 | 98 aa | QLISS family |
| | Rv2348c | 2626655-2626978 | 108 aa | Unknown |
| | plcC | 2627173-2628696 | 508 aa | Phospholipase |
| | plcB | 2628782-2630317 | 512 aa | Phospholipase |
| | plcA | 2630538-2632073 | 512 aa | Phospholipase |
| | Rv2352c | 2632924-2634096 | 391 aa | PPE protein |
| | Rv2353c | 2634529-2635590 | 354 aa | PPE protein |
| RD6 | Rv3425 | 3842235-3842762 | 176 aa | PPE protein |
| | Rv3426 | 3843032-3843727 | 232 aa | PPE protein |
| | Rv3427c | 3843884-3844636 | 251 aa | Transposase IS1532 |
| | Rv3428c | 3844737-3845966 | 410 aa | Transposase IS1532 |
| RD7 | Rv1964 | 2207698-2208492 | 265 aa | Integral membrane |
| | Rv1965 | 2208505-2209317 | 271 aa | Integral membrane |
| | Mce3 | 2209325-2210599 | 425 aa | Invasin-type protein, RGD motif |
| | Rv1967 | 2210599-2211624 | 342 aa | Exported protein |
| | Rv1968 | 2211624-2212853 | 410 aa | Exported protein, RGD motif |
| | Rv1969 | 2212853-2214122 | 423 aa | Exported protein |
| | lprM | 2212853-2214122 | 377 aa | Lipoprotein |
| | Rv1971 | 2215255-2216565 | 437 aa | Exported protein |
| | Rv1972 | 2216590-2217162 | 191 aa | Membrane protein |

TABLE 1-continued

DESCRIPTION OF THE DELETIONS

| DELE-TIONS | ORF/GENE | POSITION ® ON THE GENOME OF M. TUBERCULOSIS H37RV | SIZE OF THE PRODUCT | PUTATIVE FUNCTION OR FAMILY |
|---|---|---|---|---|
|  | Rv1973 | 2217162-2217641 | 160 aa | Exported protein |
|  | Rv1974 | 2217657-2218031 | 125 aa | Unknown |
|  | Rv1975 | 2218050-2218712 | 221 aa | Exported protein |
|  | Rv1976c | 2218845-2219249 | 135 aa | Unknown |
|  | Rv1977 | 2219752-2220795 | 348 aa | Unknown, Zn binding signature |
| RD8 | ephA | 4057730-4058695 | 322 aa | Epoxide hydrolase |
|  | Rv3618 | 4058695-4059879 | 395 aa | Monooxygenase |
|  | Rv3619c | 4059984-4060265 | 94 aa | ESAT-6 family |
|  | Rv3620c | 4060295-4060588 | 98 aa | QLISS family |
|  | Rv3621c | 4060648-4061886 | 413 aa | PPE protein |
|  | Rv3622c | 4061899-4062195 | 99 aa | PE protein |
|  | lpqG | 4062524-4063243 | 240 aa | Lipoprotein |
| RD9 | cobL | 2328975-2330144 | 390 aa | Precorrin methylase |
|  | Rv2073c | 2330215-2330961 | 249 aa | Oxidoreductase |
|  | Rv2074 | 2330991-2331401 | 137 aa | Unknown |
|  | Rv2075 | 2331417-2332877 | 487 aa | Exported protein or membrane |
| RD10 | echAI | 265505-266290 | 262 aa | Enoyl-CoA hydratase |
|  | Rv0223c | 266302-267762 | 487 aa | Aldehyde dehydrogenase |
| RvD1 | RvD1-ORF1 | — | 675 aa | Unknown |
|  | RvD1-ORF2 | — | 318 aa | Unknown |
|  | Rv2024c | — | 1606 aa | Unknown |
| RvD2 | plcD | — | 514 aa | Phospholipase |
|  | RvD2-ORF1 | — | 394 aa | Sugar transferase |
|  | RvD2-ORF2 | — | 367 aa | Oxidoreductase |
|  | RvD2-ORF3 | — | 945 aa | Membrane protein |
|  | Rv1758 | — | 143 aa | Cutinase |

* As defined by Cole et al., Nature, 1998, 393, pages 537-544

TABLE 2

DISTRIBUTION OF THE DELETIONS AMONG THE M. TUBERCULOSIS COMPLEX

| DELETION | M. tuberculosis H37Rv | M. africanum | M. bovis | M. bovis BCG | M. microti OV254 | M. tuberculosis CSU#93 | M. tuberculosis CLINICAL ISOLATES* |
|---|---|---|---|---|---|---|---|
| RD4 | ✓ | ✓ | X | X | ✓ | ✓ | 27/27 |
| RD5 | ✓ | ✓ | X | X | X | ✓ | ND |
| RD6 | ✓ | ✓ | X | X | X | X | 19/30 |
| RD7 | ✓ | ✓ | X | X | X | ✓ | 30/30 |
| RD8 | ✓ | ✓ | X | X | X | ✓ | ND |
| RD9 | ✓ | X | X | X | X | ✓ | 8/8 |
| RD10 | ✓ | ✓ | X | X | X | ✓ | 8/8 |
| RvD1 | X | ✓ | ✓ | ✓ | ✓ | ✓ | 5/7 |
| RvD2 | X | ✓ | ✓ | ✓ | ✓ | ✓ | 4/7 |

ND: Not determined:
✓ = the region is present,
X = the region is deleted
*Number of clinical isolates positive for the presence of a region

TABLE 3

PCR PRIMERS
(SEQ ID NOS: 1-18, respectively in order of appearance)

| DELETION | NAME OF THE PRIMER | SEQUENCE | EXPECTED PRODUCT SIZE |
|---|---|---|---|
| RD4* | Y277-32F | ACATGTACGAGAGACGGCATGAG | H37Rv: 1031 bp |
|  | Y277-32R | ATCCAACACGCAGCAACCAG | BCG: No product |
| RD5* | plcC-B.5P | GATTCCTGGACTGGCGTTG | H37Rv: 1623 bp |
|  | plcC-B.3P | CCACCCAAGAAACCGCAC | BCG: No product |
| RD6 | Y78-delI | ACAAAATCCCCTCGTCCCC | H37Rv: 8729 bp |
|  | Y78-del2 | ACCTGTATTCGTCGTTGCTGACC | BCG: 3801 bp |
| RD7 | Rv420-flank1.F | GGTAATCGTGGCCGACAAG | H37Rv: 13068 bp |
|  | Rv420-flank2.R | CTTGCGGCCCAATGAATC | BCG; 350 bp |
| RD8* | RD8-ephA.F | GTGTGATTTGGTGAGACGATG | H37Rv: 678 bp |
|  | RD8-ephA.R | GTTCCTCCTGACTAATCCAGGC | BCG: No product |
| RD9 | TB2329.5F | CTGCCCGTCGTGCGCGAA | H37Rv: 3048 bp |
|  | TB2332.5R | AGTGGCTCGGCACGCACA | BCG: 1018 bp |

TABLE 3-continued

PCR PRIMERS
(SEQ ID NOS: 1-18, respectively in order of appearance)

| DELE-TION | NAME OF THE PRIMER | SEQUENCE | EXPECTED PRODUCT SIZE |
|---|---|---|---|
| RD10 | RD10-264F | CGCGAAAGAGGTCATCTAAAC | H37Rv: 3024 bp |
|  | RD10-267R | GATGCTCAAGCCGTGCACC | BCG: 1121 bp |
| RvD1 | TBoli2268469.F | GCGCCACAAACGTACTATCTC | H37Rv: 595 pb |
|  | TBoli2269064.R | GTTTCACCGGCTGTCGTTC | BCG: 5595 bp |
| RvD2 | Y28-IS6110B.5' | CCACACCGCAGGATTCGCAAG | H37Rv: 2007 bp† |
|  | Y28-RHS.2 | TCGAGTGCATGAACGCAACCGA G | BCG: 7456 bp |

\* = Primers internal to the deletion
† = Size including a copy of IS6110 not present in BCG

TABLE 4

PRIMERS FOR THE IDENTIFICATION OF THE DEPLETED SAID REGIONS (SEQ ID NOS: 19-38, respectively in order of appearance)

| REGION | NAME OF THE PRIMER | SEQUENCE |
|---|---|---|
| DU1 JUNCTION | TB16.0F | GAG CCA ACG ATG ATG ATG ACC |
|  | TB16.5F | GGT CAC GGT CGG TGT CGT C |
|  | TB4398.7R | CAG AAC TGC AGG GGT GGT AC |
| DU2A JUNCTION | TB3689.5F | CTA GTT GTT CAG CCG CGT CTT |
|  | TB3591.0R | ACC GGG GTG TCG GCC AGT T |
|  | TB3689.9F | TCG CGG CCA CCG TGC GTA A |
|  | TB3591.5R | GGC GCC TAT GAC TGA TAC CC |
| DU2B JUNCTION | TB3608.0F | GAA CAG GGT CGC GGA GTC T |
|  | TB3672.0R | TCG AGG AGG TCG AGT CCT GT |
|  | TB3671.7R | GGG TTC ATG AGG TGC TAG GG |
| DETECTION PRIMERS RvD5 | RvD5-intF | GGG TTC ACG TTC ATT ACT GTT C |
|  | RvD5-intR | CCT GCG CTT ATC TCT AGC GG |
| HYBRIDI-ZATION PROBE DU1 | TB4411.0F | CCG GCC ACT CAC TGC CTT C |
|  | TB0.3R | ACG GTA GTG TCG TCG GCT TC |
| HYBRIDI-ZATION PROBE DU2 (probe 3 675) | TB3675.0F | CCA ACA CCG TCA ACT ACT CGA |
|  | TB3675.5R | ATC GCA GAA CTC CGG CGA CA |
| SEQUENCING OF THE REGION dnaA-dnaN | TB1.2F | CGA TCT GAT CGC CGA CGC C |
|  | TB1.5F | TCC GTC AGC GCT CCA AGC G |
|  | TB1.8F | GTC CCC AAA CTG CAC ACC CT |
|  | TB2.2R | AAT CCG GAA ATC GTC AGA CCG |

REFERENCES

1. Arruda, S., Bomfim, G., Knights, R., Huima, B. T. and Riley, L. W. (1993) Cloning of an *M. tuberculosis* DNA fragment associated with entry and survival inside cells. *Science* 261: 1454-1457.
2. Bloom, B. R. and Fine, P. E. M. (1994) The BCG experience: Implications for future vaccines against tuberculosis. In *Tuberculosis: Pathogenesis, Protection and Control*. Bloom, B. R. (eds). Washington D.C.: American Society for Microbiology, pp. 531-557.
3. Brosch, R., Gordon, S. V., Billault, A., Garnier, T., Eiglmeier, K., Soravito, C., Barrell, B. G. and Cole, S. T. (1998) Use of a *Mycobacterium tuberculosis* H37Rv bacterial artificial chromosome library for genome mapping, sequencing, and comparative genomics. *Infect Immun* 66: 2221-2229.
4. Calmette, A. (1927) *La vaccination contre la tuberculose*, 250 p, Paris: Masson et Cie.
5. Chee, M., Yang, R., Hubbell, E., Berno, A., Huang, X. C., Stern, D., Winkler, J., Lockhart, D. J., Morris, M. S, and Fodor, S. P. (1996) Accessing genetic information with high-density DNA arrays *Science* 274: 610-614.
6. Cole, S. T., Brosch, R., Parkhill, J., Garnier, T., Churcher, C., Harris, D. et al. (1988) Deciphering the biology of *Mycobacterium tuberculosis* from the complete genome sequence. *Nature* 393: 537-544.
7. DeRisi, J. L., Iyer, V. R. and Brown, P. O. (1997) Exploring the metabolic and genetic control of gene expression on a genomic scale. *Science* 278: 610-614.
8. Elhay, M. J., Oettinger, T. and Andersen, P. (1998) Delayed-type hypersensitivity responses to ESAT-6 and MPT64 from *Mycobacterium tuberculosis* in the guinea pig. *Infect Immun* 66: 3454-3456.
9. Fine, P. E. M. (1994) Immunities in and to tuberculosis: implications for pathogenesis and vaccination. In *Tuberculosis: Back to the future*. Porter, J. D. H. and McAdam, K. P. W. J. (eds) Chichester: John Wiley and Sons Ltd., pp. 53-74.
10. Gordon, S. V., Heym, B., Parkhill, J., Barrell, B. G. and Cole, S. T. (1998) New insertion sequences and a novel repetitive element in the genome of *Mycobacterium tuberculosis*. *Microbiology* (in press)
11. Harboe, M., Oettinger, T., Wiker, H. G., Rosenkrands, I. and Andersen, P. (1996) Evidence for occurrence of the ESAT-6 protein in *Mycobacterium tuberculosis* and virulent *Mycobacterium bovis* and for its absence in *Mycobacterium bovis* BCG. *Infect Immun* 64: 16-22.
12. Heifets, L. B. and Good, R. C. (1994) Current laboratory methods for the diagnosis of tuberculosis. In *Tuberculosis: Pathogenesis, Protection and Control*. Bllom, B. R. (eds). Washington D.C. American Society for Microbiology, pp. 85-110.
13. Horwitz, M. A., Lee, B. W., Dillon, B. J. and Harth, G. (1995) Protective immunity against tuberculosis induced by vaccination with major extracellular proteins of *Mycobacterium tuberculosis*. *Proc Natl Acad Sci USA* 92: 1530-1534.
14. Johansen, K. A., Gill, R. E. and Vasil, M. L. (1996) Biochemical and molecular analysis of phospholipase C and phospholipase D activity-in mycobacteria. *Infect Immun* 64: 3259-3266.
15. Kim, U. J., Birren, B. W., Slepak, T., Mancino, V., Boysen, C., Kang, H. L., Simon, M. I. and Shizuya, H. (1996) Construction and characterization of a human bacterial artificial chromosome library. *Genomics* 34: 213-218

16. Lagranderie, M. R., Balazuc, A. M., Deriaud, E. and Leclerc, C. D. (1996) Comparison of immune responses of mice immunized with five different *Mycobacterium bovis* vaccine strains. *Infect Immun* 64: 1-9.
17. Lawes, M. and Maloy, S. (1995) MudSacI, a transposon with strong selectable and counterselectable markers: use for rapid mapping of chromosomal mutations in *Salmonella typhimurium. J. Bacteriol* 177: 1383-1387.
18. Leao, S. C., Rocha, C. L., Murillo, L. A., Parra, C. A. and Patarroyo, M. E. (1995) A species-specific nucleotide sequence of *Mycobacterium tuberculosis* encodes a protein that exhibits hemolytic activity when expressed in *Escherichia coli. Infect Immun* 63: 4301-4306.
19. Mahairas, G. G., Sabo, P. J., Hickey, M. J., Singh, D. C. and Stover, C. K. (1996) Molecular analysis of genetic differences between *Mycobacterium bovis* BCG and virulent *M. bovis. J Bacteriol* 178: 1274-1282.
20. Moghaddam, M. F., Grant, D. F., Cheek, J. M., Greene, J. F., Williamson, K. C. and Hammock, B. D. (1997) Bioactivation of leukotoxins to their toxic diols by epoxide hydrolase. *Nature Med* 3: 562-6.
21. Ohno, S. (1995) Active sites of ligands and their receptors are made of common peptides that are also found elsewhere. *J Mol Evol* 40: 102-6.
22. Pelicic, V., Reyrat, J. M. and Gicquel, B. (1996) Expressions of the *Bacillus subtilis* sacB gene confers sucrose sensitivity on mycobacteria. *J Bacteriol* 178: 1197-9.
23. Philipp, W. J., Nair, S., Guglielmi, G., Lagranderie, M., Gicquel, B. and Cole, S. T. (1996) Physical mapping of *Mycobacterium bovis* BCG Pasteur reveals differences from the genome map of *Mycobacterium tuberculosis* H37Rv and from *M. bovis. Microbiology* 142:3135-3145.
24. Philipp, W. J., Poulet, S., Eiglmeier, K., Pascopella, L., Balasubramanian, V., Heym, B., Bergh, S., Bloom, B. R., Jacobs, W. J. and Cole, S. T. (1966) An integrated map of the genome of the tubercle bacillus, *Mycobacterium tuberculosis* H37Rv, and comparison with *Mycobacterium leprae. Proc Natl Acad Sci USA* 93: 3132-3137.
25. Relman, D. A., Domenighini, M., Tuomanen, E., Rappuoli, R. and Falkow, S. (1989) Filamentous hemagglutinin of *Bordetella pertussis*: nucleotide sequence and crucial role in adherence. *Proc Natl Acad Sci USA* 86: 2637-2641.
26. Rosenkrands, I., Rasmussen, P. B., Carnio, M., Jacobsen, S., Theisen, M. and Andersen, P. (1998) Identification and characterization of a 29-kilodalton protein from *Mycobacterium tuberculosis* culture filtrate recognized by mouse memory effector cells. *Infect Immun* 66: 2728-2735.
27. Sreevatsan, S., Pan, X., Stockbauer, K. E., Connell, N. D., Kreiswirth, B. N., Whittam, T. S, and Musser, J. M. (1997) Restricted structural genes polymorphism in the *Mycobacterium tuberculosis* complex indicates evolutionarily recent global dissemination. *Proc Natl Acad Sci USA* 94: 9869-9874.
28. Titball, R. W. (1993) Bacterial phospholipases C. *Microbiological Reviews* 57: 347-66.
29. Wheeler, P. R. and Ratledge, C. (1992) Control and location of acyl-hydrolysing phospholipase activity in pathogenic mycobacteria. *J Gen Microbiol* 138: 825-830.
30. Woo, S. S., Jiang, J., Gill, B. S., Paterson, A. H. and Wing, R. A. (1994) Construction and characterization of a bacterial artificial chromosome library of *Sorghum bicolor. Nuc Acids Res* 22: 4922-31.

---

The invention claimed is:

1. A method for discriminating *M. africanum, M. bovis* BCG, *M. bovis*, and *M. microti* OV254, from *M. tuberculosis* in a biological sample, the method comprising:

(A) bringing the biological sample into contact with primers SEQ ID NO:11 and SEQ ID NO:12;

(B) performing an amplification reaction; and (C) determining whether the biological sample contains a mycobacterium selected from *M. africanum, M. bovis* BCG, *M. bovis*, and *M. microti* OV254, or contains *M. tuberculosis* based on the length of the amplified product.

2. A method of amplifying a DNA sequence of variable length from *M. africanum, M. bovis* BCG, *M. bovis, M. microti* OV254, or *M. tuberculosis*, wherein the method comprises:

hybridizing SEQ ID NO:11 and SEQ ID NO:12 to the DNA sequence; and performing an amplification reaction, wherein the length of the amplified product from *M. africanum, M. bovis* BCG, *M. bovis*, and *M. microti* OV254 is shorter than the length of the amplified product from *M. tuberculosis.*

3. A method for discriminating *M. bovis* BCG, *M. bovis, M. africanum*, and *M. microti* OV254, from *M. tuberculosis* in a biological sample, the method comprising:

(A) bringing the biological sample into contact with primers SEQ ID NO:11 and SEQ ID NO:12;

(B) performing an amplification reaction; and (C) determining whether the biological sample contains one or more of *M. africanum, M. bovis* BCG, *M. bovis*, and *M. microti* OV254, or contains *M. tuberculosis* based on the sequence or on the length of the amplified product.

4. The method of claim 3, wherein the step of determining whether the biological sample contains one or more of *M. bovis* BCG, *M. bovis, M. africanum*, and *M. microti* OV254, or contains *M. tuberculosis* comprises determining whether the amplified product comprises at least one *M. tuberculosis* open reading frame chosen from Rv2073c and Rv2074, and/or a truncation of at least one *M. tuberculosis* open reading frame chosen from cobL and Rv2075, wherein said truncation occurs within the RD9 region from the *M. tuberculosis* H37Rv genome.

5. A method for discriminating *M. bovis* BCG, *M. bovis, M. africanum*, and *M. microti* OV254, from *M. tuberculosis* in a biological sample, the method comprising:

(A) isolating DNA from the biological sample or producing cDNA from RNA of the biological sample;

(B) detecting the presence/absence of the RD9 region from the *M. tuberculosis* H37Rv genome in the DNA or cDNA; and (C) determining that the biological sample contains one or more of *M. africanum, M. bovis* BCG, *M. bovis*, and *M. microti* OV254 if the RD9 region from the *M. tuberculosis* H37Rv genome is absent from the DNA or cDNA, or that the biological sample contains *M. tuberculosis* if the RD9 region is present in the DNA or cDNA;

wherein the detecting comprises performing an amplification reaction with primers SEQ ID NO:11 and SEQ ID NO:12.

6. The method of claim 5, wherein the absence of the RD9 region is detected by determining whether at least one *M. tuberculosis* open reading frame chosen from Rv2073c and Rv2074 is absent from the DNA or cDNA, and/or whether the DNA or cDNA comprises a truncation of at least one *M. tuberculosis* open reading frame chosen from cobL and Rv2075, wherein said truncation occurs within the RD9 region from the *M. tuberculosis* H37Rv genome.

7. The method of claim 5, further comprising examining the length of the amplified product.

8. The method of claim 5, further comprising examining the sequence of the amplified product.

9. The method of claim 8, wherein the sequence of the amplified product is examined to determine if it contains at least one *M. tuberculosis* open reading frame chosen from Rv2073c and Rv2074, and/or a truncation of at least one *M. tuberculosis* open reading frame chosen from cobL and Rv2075, wherein said truncation occurs within the RD9 region from the *M. tuberculosis* H37Rv genome.

* * * * *

SEQUENCE LISTING

```
<160> NUMBER OF SEQ ID NOS: 54

<210> SEQ ID NO 1
<211> LENGTH: 24
<212> TYPE: DNA
<213> ORGANISM: Mycobacterium tuberculosis
<220> FEATURE:
<223> OTHER INFORMATION: Y277-32F

<400> SEQUENCE: 1
gacatgtacg agagacggca tgag                                          24

<210> SEQ ID NO 2
<211> LENGTH: 21
<212> TYPE: DNA
<213> ORGANISM: Mycobacterium tuberculosis
<220> FEATURE:
<223> OTHER INFORMATION: Y277-32R

<400> SEQUENCE: 2
aatccaacac gcagcaacca g                                             21

<210> SEQ ID NO 3
<211> LENGTH: 20
<212> TYPE: DNA
<213> ORGANISM: Mycobacterium tuberculosis
<220> FEATURE:
<223> OTHER INFORMATION: plcC-B.5P

<400> SEQUENCE: 3
ggattcctgg actggcgttg                                               20
```

<210> SEQ ID NO 4
<211> LENGTH: 19
<212> TYPE: DNA
<213> ORGANISM: Mycobacterium tuberculosis
<220> FEATURE:
<223> OTHER INFORMATION: plcC-B.3P

<400> SEQUENCE: 4
cccacccaag aaaccgcac                                                  19

<210> SEQ ID NO 5
<211> LENGTH: 20
<212> TYPE: DNA
<213> ORGANISM: Mycobacterium tuberculosis
<220> FEATURE:
<223> OTHER INFORMATION: Y78-del1

<400> SEQUENCE: 5
acaaaaatcg cctcgtcgcc                                                 20

<210> SEQ ID NO 6
<211> LENGTH: 24
<212> TYPE: DNA
<213> ORGANISM: Mycobacterium tuberculosis
<220> FEATURE:
<223> OTHER INFORMATION: Y78-del2

<400> SEQUENCE: 6
aacctgtatt cgtcgttgct gacc                                            24

<210> SEQ ID NO 7
<211> LENGTH: 20
<212> TYPE: DNA
<213> ORGANISM: Mycobacterium tuberculosis
<220> FEATURE:
<223> OTHER INFORMATION: Rv420-flank1.F

<400> SEQUENCE: 7
tggtaatcgt ggccgacaag                                                 20

<210> SEQ ID NO 8
<211> LENGTH: 19
<212> TYPE: DNA
<213> ORGANISM: Mycobacterium tuberculosis
<220> FEATURE:
<223> OTHER INFORMATION: RV420-flank2.R

<400> SEQUENCE: 8
tcttgcggcc caatgaatc                                                  19

<210> SEQ ID NO 9
<211> LENGTH: 22
<212> TYPE: DNA
<213> ORGANISM: Mycobacterium tuberculosis
<220> FEATURE:
<223> OTHER INFORMATION: RD8-ephA.F

<400> SEQUENCE: 9
ggtgtgattt ggtgagacga tg                                              22

<210> SEQ ID NO 10
<211> LENGTH: 23
<212> TYPE: DNA
<213> ORGANISM: Mycobacterium tuberculosis
<220> FEATURE:
<223> OTHER INFORMATION: RD8-ephA.R

```
<400> SEQUENCE: 10
agttcctcct gactaatcca ggc                                              23

<210> SEQ ID NO 11
<211> LENGTH: 19
<212> TYPE: DNA
<213> ORGANISM: Mycobacterium tuberculosis
<220> FEATURE:
<223> OTHER INFORMATION: TB2329.5F

<400> SEQUENCE: 11
tctgcccgtc gtgcgcgaa                                                   19

<210> SEQ ID NO 12
<211> LENGTH: 19
<212> TYPE: DNA
<213> ORGANISM: Mycobacterium tuberculosis
<220> FEATURE:
<223> OTHER INFORMATION: TB2332.5R

<400> SEQUENCE: 12
cagtggctcg gcacgcaca                                                   19

<210> SEQ ID NO 13
<211> LENGTH: 22
<212> TYPE: DNA
<213> ORGANISM: Mycobacterium tuberculosis
<220> FEATURE:
<223> OTHER INFORMATION: RD10-264F

<400> SEQUENCE: 13
tcgcgaaaga ggtcatctaa ac                                               22

<210> SEQ ID NO 14
<211> LENGTH: 20
<212> TYPE: DNA
<213> ORGANISM: Mycobacterium tuberculosis
<220> FEATURE:
<223> OTHER INFORMATION: DR10-267R

<400> SEQUENCE: 14
agatgctcaa gccgtgcacc                                                  20

<210> SEQ ID NO 15
<211> LENGTH: 22
<212> TYPE: DNA
<213> ORGANISM: Mycobacterium bovis
<220> FEATURE:
<223> OTHER INFORMATION: TBoli2268469.F

<400> SEQUENCE: 15
cgcgccacaa acgtactatc tc                                               22

<210> SEQ ID NO 16
<211> LENGTH: 20
<212> TYPE: DNA
<213> ORGANISM: Mycobacterium bovis
<220> FEATURE:
<223> OTHER INFORMATION: TBoli2269064.R

<400> SEQUENCE: 16
agtttcaccg gctgtcgttc                                                  20

<210> SEQ ID NO 17
<211> LENGTH: 22
```

-continued

```
<212> TYPE: DNA
<213> ORGANISM: Mycobacterium bovis
<220> FEATURE:
<223> OTHER INFORMATION: Y28-IS6110B.5

<400> SEQUENCE: 17
cccacaccgc aggattggca ag                                              22

<210> SEQ ID NO 18
<211> LENGTH: 24
<212> TYPE: DNA
<213> ORGANISM: Mycobacterium bovis
<220> FEATURE:
<223> OTHER INFORMATION: Y28-RHS.2

<400> SEQUENCE: 18
atcgagtgca tgaacgcaac cgag                                            24

<210> SEQ ID NO 19
<211> LENGTH: 21
<212> TYPE: DNA
<213> ORGANISM: Mycobacterium bovis
<220> FEATURE:
<223> OTHER INFORMATION: BCG strain: TB16.0F

<400> SEQUENCE: 19
gagccaacga tgatgatgac c                                               21

<210> SEQ ID NO 20
<211> LENGTH: 19
<212> TYPE: DNA
<213> ORGANISM: Mycobacterium bovis
<220> FEATURE:
<223> OTHER INFORMATION: BCG strain: TB16.5F

<400> SEQUENCE: 20
ggtcacggtc ggtgtcgtc                                                  19

<210> SEQ ID NO 21
<211> LENGTH: 20
<212> TYPE: DNA
<213> ORGANISM: Mycobacterium bovis
<220> FEATURE:
<223> OTHER INFORMATION: BCG strain: TB4398.7R

<400> SEQUENCE: 21
cagaactgca ggggtggtac                                                 20

<210> SEQ ID NO 22
<211> LENGTH: 21
<212> TYPE: DNA
<213> ORGANISM: Mycobacterium bovis
<220> FEATURE:
<223> OTHER INFORMATION: BCG strain: TB3689.5

<400> SEQUENCE: 22
ctagttgttc agccgcgtct t                                               21

<210> SEQ ID NO 23
<211> LENGTH: 19
<212> TYPE: DNA
<213> ORGANISM: Mycobacterium bovis
<220> FEATURE:
<223> OTHER INFORMATION: BCG strain: TB3591.0R

<400> SEQUENCE: 23
accggggtgt cggccagtt                                                  19
```

<210> SEQ ID NO 24
<211> LENGTH: 19
<212> TYPE: DNA
<213> ORGANISM: Mycobacterium bovis
<220> FEATURE:
<223> OTHER INFORMATION: BCG strain: TB3689.9F

<400> SEQUENCE: 24
tcgcggccac cgtgcgtaa                                            19

<210> SEQ ID NO 25
<211> LENGTH: 20
<212> TYPE: DNA
<213> ORGANISM: Mycobacterium bovis
<220> FEATURE:
<223> OTHER INFORMATION: BCG strain: TB3591.5R

<400> SEQUENCE: 25
ggcgcctatg actgataccc                                           20

<210> SEQ ID NO 26
<211> LENGTH: 19
<212> TYPE: DNA
<213> ORGANISM: Mycobacterium bovis
<220> FEATURE:
<223> OTHER INFORMATION: BCG strain: TB3608.0F

<400> SEQUENCE: 26
gaacagggtc gcggagtct                                            19

<210> SEQ ID NO 27
<211> LENGTH: 20
<212> TYPE: DNA
<213> ORGANISM: Mycobacterium bovis
<220> FEATURE:
<223> OTHER INFORMATION: BCG strain: TB3672.0R

<400> SEQUENCE: 27
tcgaggaggt cgagtcctgt                                           20

<210> SEQ ID NO 28
<211> LENGTH: 20
<212> TYPE: DNA
<213> ORGANISM: Mycobacterium bovis
<220> FEATURE:
<223> OTHER INFORMATION: BCG strain: TB3671.7R

<400> SEQUENCE: 28
gggttcatga ggtgctaggg                                           20

<210> SEQ ID NO 29
<211> LENGTH: 22
<212> TYPE: DNA
<213> ORGANISM: Mycobacterium bovis
<220> FEATURE:
<223> OTHER INFORMATION: BCG strain: RvD5-intF

<400> SEQUENCE: 29
gggttcacgt tcattactgt tc                                        22

<210> SEQ ID NO 30
<211> LENGTH: 20
<212> TYPE: DNA
<213> ORGANISM: Mycobacterium bovis
<220> FEATURE:
<223> OTHER INFORMATION: BCG strain: RvD5-intR

<400> SEQUENCE: 30
cctgcgctta tctctagcgg 20

<210> SEQ ID NO 31
<211> LENGTH: 19
<212> TYPE: DNA
<213> ORGANISM: Mycobacterium bovis
<220> FEATURE:
<223> OTHER INFORMATION: BCG strain: TB4411.0F

<400> SEQUENCE: 31
ccggccactc actgccttc 19

<210> SEQ ID NO 32
<211> LENGTH: 20
<212> TYPE: DNA
<213> ORGANISM: Mycobacterium bovis
<220> FEATURE:
<223> OTHER INFORMATION: BCG strain: TB0.3R

<400> SEQUENCE: 32
acggtagtgt cgtcggcttc 20

<210> SEQ ID NO 33
<211> LENGTH: 21
<212> TYPE: DNA
<213> ORGANISM: Mycobacterium bovis
<220> FEATURE:
<223> OTHER INFORMATION: BCG strain: TB3675.0F

<400> SEQUENCE: 33
ccaacaccgt caactactcg a 21

<210> SEQ ID NO 34
<211> LENGTH: 20
<212> TYPE: DNA
<213> ORGANISM: Mycobacterium bovis
<220> FEATURE:
<223> OTHER INFORMATION: BCG strain: TB3675.5R

<400> SEQUENCE: 34
atcgcagaac tccggcgaca 20

<210> SEQ ID NO 35
<211> LENGTH: 19
<212> TYPE: DNA
<213> ORGANISM: Mycobacterium bovis
<220> FEATURE:
<223> OTHER INFORMATION: BCG strain: TB1.2F

<400> SEQUENCE: 35
cgatctgatc gccgacgcc 19

<210> SEQ ID NO 36
<211> LENGTH: 19
<212> TYPE: DNA
<213> ORGANISM: Mycobacterium bovis
<220> FEATURE:
<223> OTHER INFORMATION: BCG strain: TB1.5F

<400> SEQUENCE: 36
tccgtcagcg ctccaagcg 19

<210> SEQ ID NO 37
<211> LENGTH: 20

<212> TYPE: DNA
<213> ORGANISM: Mycobacterium bovis
<220> FEATURE:
<223> OTHER INFORMATION: BCG strain: TB1.8F

<400> SEQUENCE: 37
gtccccaaac tgcacaccct 20

<210> SEQ ID NO 38
<211> LENGTH: 21
<212> TYPE: DNA
<213> ORGANISM: Mycobacterium bovis
<220> FEATURE:
<223> OTHER INFORMATION: BCG strain: TB2.2R

<400> SEQUENCE: 38
aatccggaaa tcgtcagacc g 21

<210> SEQ ID NO 39
<211> LENGTH: 19
<212> TYPE: DNA
<213> ORGANISM: Mycobacterium tuberculosis

<400> SEQUENCE: 39
aagtcacccg cggccaaca 19

<210> SEQ ID NO 40
<211> LENGTH: 19
<212> TYPE: DNA
<213> ORGANISM: Mycobacterium tuberculosis

<400> SEQUENCE: 40
aaactcgagt ttatgtttc 19

<210> SEQ ID NO 41
<211> LENGTH: 14
<212> TYPE: DNA
<213> ORGANISM: Mycobacterium tuberculosis

<400> SEQUENCE: 41
attggacaac gcgg 14

<210> SEQ ID NO 42
<211> LENGTH: 14
<212> TYPE: DNA
<213> ORGANISM: Mycobacterium tuberculosis

<400> SEQUENCE: 42
taagtccgtg tcgg 14

<210> SEQ ID NO 43
<211> LENGTH: 15
<212> TYPE: DNA
<213> ORGANISM: Mycobacterium tuberculosis

<400> SEQUENCE: 43
accgtgaacc aaagc 15

<210> SEQ ID NO 44
<211> LENGTH: 14
<212> TYPE: DNA
<213> ORGANISM: Mycobacterium tuberculosis

<400> SEQUENCE: 44
cgtgggacgg gcag 14

-continued

<210> SEQ ID NO 45
<211> LENGTH: 10
<212> TYPE: DNA
<213> ORGANISM: Mycobacterium tuberculosis

<400> SEQUENCE: 45
ttgcgaggca 10

<210> SEQ ID NO 46
<211> LENGTH: 14
<212> TYPE: DNA
<213> ORGANISM: Mycobacterium tuberculosis

<400> SEQUENCE: 46
atgaaccaga ccaa 14

<210> SEQ ID NO 47
<211> LENGTH: 13
<212> TYPE: DNA
<213> ORGANISM: Mycobacterium tuberculosis

<400> SEQUENCE: 47
aattactgtg gcc 13

<210> SEQ ID NO 48
<211> LENGTH: 14
<212> TYPE: DNA
<213> ORGANISM: Mycobacterium tuberculosis

<400> SEQUENCE: 48
cacgccgggc cggg 14

<210> SEQ ID NO 49
<211> LENGTH: 16
<212> TYPE: DNA
<213> ORGANISM: Mycobacterium tuberculosis

<400> SEQUENCE: 49
ccgacgttca tgaatc 16

<210> SEQ ID NO 50
<211> LENGTH: 15
<212> TYPE: DNA
<213> ORGANISM: Mycobacterium tuberculosis

<400> SEQUENCE: 50
ggataaagaa gcctt 15

<210> SEQ ID NO 51
<211> LENGTH: 13
<212> TYPE: DNA
<213> ORGANISM: Mycobacterium tuberculosis

<400> SEQUENCE: 51
aagaattcaa aca 13

<210> SEQ ID NO 52
<211> LENGTH: 15
<212> TYPE: DNA
<213> ORGANISM: Mycobacterium tuberculosis

<400> SEQUENCE: 52
cgccaggccc gggcc 15

-continued

```
<210> SEQ ID NO 53
<211> LENGTH: 14
<212> TYPE: DNA
<213> ORGANISM: Mycobacterium tuberculosis

<400> SEQUENCE: 53
ccggcatcgc taag                                                    14

<210> SEQ ID NO 54
<211> LENGTH: 13
<212> TYPE: DNA
<213> ORGANISM: Mycobacterium tuberculosis

<400> SEQUENCE: 54
gaggacttca tcg                                                     13
```